United States Patent [19]
Seitz et al.

[11] Patent Number: 5,925,595
[45] Date of Patent: Jul. 20, 1999

[54] MICROCAPSULES WITH READILY ADJUSTABLE RELEASE RATES

[75] Inventors: Michael E. Seitz; Ronald J. Brinker, both of Ellisville; Jeff N. Travers, Chesterfield, all of Mo.

[73] Assignee: Monsanto Company, St. Louis, Mo.

[21] Appl. No.: 08/924,671

[22] Filed: Sep. 5, 1997

[51] Int. Cl.⁶ .................................................. A01N 25/28
[52] U.S. Cl. ...................... 504/116; 424/405; 514/963; 504/342
[58] Field of Search .................... 504/116, 342; 424/405; 514/963

[56] References Cited

U.S. PATENT DOCUMENTS

| | | | |
|---|---|---|---|
| 4,280,833 | 7/1981 | Beestman et al. | 71/100 |
| 4,285,720 | 8/1981 | Scher | 71/88 |
| 4,417,916 | 11/1983 | Beestman et al. | 71/93 |
| 4,643,764 | 2/1987 | Scher | 71/100 |
| 4,847,152 | 7/1989 | Jabs et al. | 428/402.21 |
| 5,049,182 | 9/1991 | Scher et al. | 71/93 |
| 5,073,191 | 12/1991 | Misselbrook et al. | 71/121 |
| 5,160,530 | 11/1992 | Misselbrook et al. | 71/121 |
| 5,223,477 | 6/1993 | Scher et al. | 504/112 |
| 5,317,004 | 5/1994 | Misselbrook et al. | 504/116 |
| 5,342,556 | 8/1994 | Träubel et al. | 264/4.7 |
| 5,461,027 | 10/1995 | Bergman | 504/247 |
| 5,552,365 | 9/1996 | Berneth et al. | 503/213 |
| 5,556,583 | 9/1996 | Tashiro et al. | 264/4.1 |
| 5,583,090 | 12/1996 | Stern et al. | 504/140 |
| 5,597,557 | 1/1997 | Kumar et al. | 424/70.17 |
| 5,597,780 | 1/1997 | Lee et al. | 504/271 |

OTHER PUBLICATIONS

Higuchi, "Mechanism of Sustained–Action Medication, Theoretical Analysis of Rate of Release of Solid Drugs Dispersed in Solid Matrices," Journal of Pharmaceutical Sciences, vol. 52, No. 12, pp. 1145–1149 (Dec. 1963).

Omi et al., "Controlled Release of Water–Soluble Drugs from Hollow Spheres: Experiments and Model Analysis," Microencapsulation of Drugs, pp. 81–101 (Whately, T., ed.; Harwood Academic Publishers 1992).

*Primary Examiner*—S. Mark Clardy
*Attorney, Agent, or Firm*—Jon H. Beusen; Arnold, White & Durkee

[57] ABSTRACT

A process for the preparation of a microencapsulated composition comprises: (a) combining (i) a triisocyanate that is an adduct of linear aliphatic isocyanates having the formula $O{=}C{=}N{-}(CH_2)_n{-}N{=}C{=}O$, where n is from about 4–18, (ii) an aliphatic diisocyanate that contains a cycloaliphatic or aromatic ring moiety, the aliphatic diisocyanate having from about 6–32 carbon atoms, most preferably from about 8–18 carbon atoms, and (iii) a water-immiscible composition comprising a core chemical; (b) adding an aqueous liquid and forming an oil-in-water emulsion; (c) adding a polyamine to the emulsion; and (d) reacting the triisocyanate, the diisocyanate, and the polyamine, thereby producing a plurality of microcapsules having a capsule wall, with at least a major portion of the core chemical encapsulated within the capsule wall of the microcapsules. Suitable core chemicals include agricultural chemicals such as herbicides and safeners. By adjusting the composition of the capsule walls and the contents of the capsule core, the rate of release of the core materials from the microcapsules can be adjusted. When the core contains two or more materials to be released, the microcapsules can provide a more rapid rate of release for one core material than for another.

99 Claims, 5 Drawing Sheets

MICROCAPSULES WITH READILY ADJUSTABLE RELEASE RATES

BACKGROUND OF THE INVENTION

The present invention relates to microencapsulated compositions of agricultural chemicals, particularly herbicides. This invention also relates to microcapsules that provide a controlled rate of release of their contents.

Controlled release for biologically active materials has been a topic of intense interest for the agricultural industry. Controlled release delivery systems offer the promise of reductions in pesticide usage and in volatility losses. Pesticide leaching into ground water, a serious problem for all-at-once methods of delivery typically used with emulsifiable and suspension concentrates, could be significantly reduced by a delivery system that provided controlled release. Product toxicity could be improved, and better crop safety achieved. These advantages have led to the development of a number of formulations involving microcapsules and microspheres.

A number of microencapsulation techniques have been developed, and a wide variety of them are used extensively in the graphic arts and pharmaceutical industries. In the agricultural field, however, most commercial techniques are limited to polyurea shell walls formed by interfacial polymerization. Aromatic isocyanates are used exclusively with either a polyamine crosslinker (Beestman, U.S. Pat. No. 4,280,833) or another aromatic isocyanate that is hydrolyzed in-situ to produce the amine (Scher, U.S. Pat. No. 4,643,764). These processes are simple and moderately successful. However these rigid, microporous capsules have not fully realized the promise of controlled release.

The release mechanisms of these polyurea microcapsules are poorly defined. The escape of core material from the capsule has been described as either diffusion through the microporous shell wall or rupture induced by environmental stress. The only practical means of adjusting the release rate from these microcapsules is by modifying the wall thickness or particle size.

Reducing the wall thickness to increase the release rate has definite limitations. The thin walls produced are sensitive to premature mechanical rupture during handling or in the field, resulting in immediate release. Poor package stability can also arise when the core material (i.e., the material inside the shell wall) is in direct contact with the external vehicle through wall defects. Some core materials may crystallize outside the capsule causing problems in spray applications. The product becomes little more than an emulsion stabilized against coalescence. When delivered to the field, the release is so fast that little is gained over traditional emulsion concentrate formulations.

If the wall thickness is increased, the bioefficacy quickly drops to a marginal performance level. There is also a practical limit to the wall thickness in interfacial polymerization. As the polymer precipitates, the reaction becomes diffusion controlled. The reaction rate can drop to such an extent that non-constructive side reactions can predominate. Hydrolysis of the isocyanate by residual moisture in the core is one of the more common side reactions. Since this reaction is not interfacial, there is no assurance that this polymerization contributes to wall formation.

Adjusting the release by changing the particle size suffers from most of the problems associated with changing wall thickness. In one sense, it is simply an indirect means of adjusting wall thickness. Additionally, interfacial polymerization techniques are ideally suited for production of capsules in the 2 to 12 micron range. The release rate does not vary significantly between these two extremes. The limited difference in release rate is further muted by the averaging effects of broadening size distributions that inevitably occur as the size is increased.

These prior art microencapsulation procedures are thus adequate for producing very fast release rates or very slow release rates. The practitioner of this art has great difficulty optimizing the release rates to obtain maximum bioefficacy for a given active ingredient (e.g., a herbicide). Various formulation solutions have been attempted to address this limitation. Two package or single package blends of microcapsules and dispersions or emulsions of free agricultural actives have been proposed (Scher, U.S. Pat. Nos. 5,223,477 and 5,049,182). It is one of the purposes of this invention to provide a microcapsule whose release mechanism and rate are reliable and readily adjustable.

SUMMARY OF THE INVENTION

One aspect of the present invention is a process for the preparation of a microencapsulated composition. The process comprises:

(a) combining (i) a triisocyanate that is an adduct of linear aliphatic isocyanates having the formula

$$O=C=N-(CH_2)_n-N=C=O \qquad (1)$$

where n is from about 4–18, (ii) an aliphatic diisocyanate that contains a cycloaliphatic or aromatic ring moiety, the aliphatic diisocyanate having from about 6–32 carbon atoms, most preferably from about 8–18 carbon atoms, and (iii) a water-immiscible composition comprising a core chemical;

(b) adding an aqueous liquid and forming an oil-in-water emulsion;

(c) adding a polyamine to the emulsion; and (d) reacting the triisocyanate, the diisocyanate, and the polyamine, thereby producing a plurality of microcapsules having a capsule wall, with at least a major portion of the core chemical encapsulated within the capsule wall of the microcapsules.

"A major portion" in this context means that more than about 50% by weight of the core chemical added in step (a) ultimately is encapsulated within the capsule wall. Preferably, more than about 75% by weight of the core chemical is encapsulated, and most preferably, more than about 90%.

The reaction of step (d) preferably is performed by heating the mixture until the isocyanate infrared absorption peak at 2270 cm$^{-1}$ substantially disappears. "Substantially" in this context means that at least about 90% of the area under the peak has disappeared, most preferably at least about 95%. The mixture can be heated to a temperature between about 40–60° C. for between about 0.5–3 hours.

In one embodiment of the invention, the core chemical comprises at least one agricultural chemical. Suitable agricultural chemicals include, for example, pesticides such as herbicides, insecticides, and funcigides; plant growth regulators; safeners; fertilizers; and plant nutrients. In one preferred embodiment, the agricultural chemical comprises a herbicide. Acetanilides such as alachlor, acetochlor, and butachlor are particularly preferred.

In another preferred embodiment, the water-immiscible composition comprises a first agricultural chemical such as a herbicide and a second agricultural chemical, such as a safener.

The triisocyanate preferably has the formula

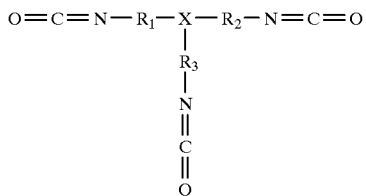

where $R_1$, $R_2$, and $R_3$ are independently alkyl groups having from 1–18 carbon atoms; and where X is a coupling agent selected from the group consisting of a tertiary carbon, a polycarbodiimide, a polyurethane derived from an aliphatic alcohol or polyol, or a combination thereof. The molecular weight of the coupling agent X is preferably less than 500. X is most preferably a homopolymer or trimer of hexamethylene diisocyanate, made by a coupling reaction with water, alcohol, polyol, carboxylic acid, or amine.

In one particular embodiment, the triisocyanate has the formula

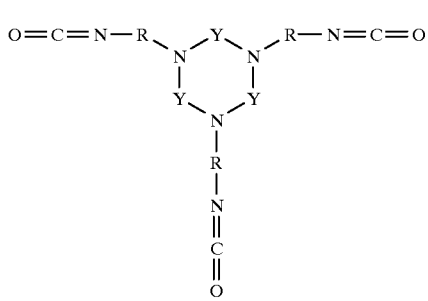

where each R group is independently an alkyl group having 1–18 carbon atoms, and where Y is a group comprising a carbonyl moiety and having from 1–6 carbon atoms.

The diisocyanate preferably has the formula

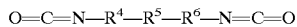

where $R^4$ and $R^6$ are independently aliphatic groups having 0–6 carbon atoms, and where $R^5$ comprises at least one substituted or unsubstituted cycloaliphatic or aromatic group that has from 5–13, most preferably from 5–6 carbon atoms. If $R^5$ comprises a polyring group, the ring moieties can be attached directly to each other or through a methylene group.

The ratio of triisocyanate to diisocyanate preferably is selected to provide a desired release rate from the microcapsules. In one embodiment, the ratio of the triisocyanate to the diisocyanate, on an isocyanate equivalent basis, is between about 90:10 and about 30:70. The core chemical can optionally have combined with it a hydrophobic diluent, such as a paraffinic oil having from about 12–28 carbon atoms, an alkylated biphenyl, or a naphthalene. The presence of such a hydrophobic diluent tends to maximize the percentage of the core chemical that will be released from the microcapsule. In other words, the hydrophobic diluent serves as a sacrificial replacement for what otherwise would be trapped core chemical.

One particular embodiment of the invention is a process for the preparation of a microencapsulated herbicidal composition, comprising:

(a) combining (i) a triisocyanate as described above, (ii) an aliphatic diisocyanate as described above, and (iii) a water-immiscible composition comprising a herbicide;

(b) dispersing the mixture from step (a) in an aqueous liquid that contains a colloid, forming an oil-in-water emulsion;

(c) adding a polyamine to the emulsion; and (d) heating the mixture from step (c) at a temperature above about 40° C., thereby producing a plurality of microcapsules having a capsule wall, with at least a major portion of the agricultural chemical encapsulated within the capsule wall of the microcapsules.

The colloid used in step (b) can be selected from the group consisting of gelatin, casein, polyvinyl alcohol, alkylated polyvinyl pyrrolidone polymers, maleic anhydride-methyl vinyl ether copolymers, styrene-maleic anhydride copolymers, maleic acid-butadiene copolymers, maleic anhydride-diisobutylene copolymers, sodium and calcium lignosulfates, sulfonated naphthalene-formaldehyde condensates, modified starches, and modified cellulose (such as the water soluble ethers produced by reacting the polymers with ethylene oxide, propylene oxide, or other alkyl oxides).

Another aspect of the invention is a selective-release microencapsulated composition that comprises a plurality of microcapsules, the microcapsules comprising (a) a capsule wall that comprises the polymerization product of a triisocyanate as described above, an aliphatic diisocyanate as described above, and a polyamine as described above, and (b) an internal phase encapsulated within the capsule wall. The internal phase comprises a first core chemical (such as a herbicide) and a second core chemical (such as a safener). Due to the nature of the capsule wall, the first core chemical has a different rate of release from the microcapsules than the second core chemical.

One embodiment of this aspect of the present invention is a microencapsulated herbicide composition, comprising a plurality of microcapsules. Each microcapsule comprises (a) a capsule wall as described above; and (b) an internal phase that comprises a herbicide and is encapsulated within the capsule wall.

Another aspect of the present invention is a herbicidal method. The method comprises applying to a plant, soil, or a growth medium a herbicidally effective amount of a composition that comprises an aqueous dispersion of microcapsules. The microcapsules each comprise a capsule wall as described above, and an internal phase that comprises a herbicide and is encapsulated within the capsule wall.

One embodiment of the herbicidal method of the present invention can control weeds while protecting valuable crops in the same field from herbicidal effects. In this method, a composition is applied to a field containing both weeds and crops in an amount effective to provide herbicidal control of the weeds. The composition comprises a plurality of microcapsules which have a capsule wall and an internal phase as described above. The internal phase in this embodiment comprises a herbicide and a safener (also referred to as a chemical antidote for the herbicide). The safener protects the crop but not the weeds from the effects of the herbicide. Due to the nature of the capsule wall, the safener can be released from the microcapsules at a greater initial rate than the herbicide, thus enhancing the protection of the corps. Two possible ways to achieve or enhance this differential rate of release are (1) using a safener that is more soluble in the capsule wall than the herbicide is, or (2) using a safener that has a smaller molecular size than the herbicide.

In general, a simple method has been found to produce a polyurea shell wall whose permeability can be readily adjusted to control release. The degree of permeability is regulated by a simple compositional change in the wall's precursors that modifies the segmental mobility of polymeric wall. This is accomplished by using a blend of two aliphatic isocyanates. One isocyanate (the triisocyanate) introduces the flexible segment into the wall while the other (the diisocyanate) introduces a rigid one. The ratio of the two isocyanates employed defines the permeability of the wall, and therefore the release rate of the microcapsule. The isocyanates used should be aliphatic to avoid the interfering side reaction effects of hydrolysis. Blends of aromatic and aliphatic isocyanates are not preferred because the reaction rate difference between them does not readily produce a homogeneous wall.

The present invention provides further benefits when two or more components are encapsulated within the shell wall of the microcapsule. The two components contained in the core can be released at different rates, depending on their solubility and molecular size. This property has particular significance when the two components encapsulated are a herbicide and a safener. The addition of a safener such as Furilazole [CA Index Name: Oxazolidine, 3-(dichloroacetyl)-5-(2-furanyl)-2,2-dimethyl-, (±)-(9CI); CA Number 141980-03-2) to acetochlor at a 60 to 1 weight ratio in the capsule core results in an effective safener/herbicide ratio of 20 to 1 outside the capsule during the initial stages of release. The safener is released at a faster rate than the herbicide from the shell walls in this embodiment, and improved crop safety results. Thus, the present invention provides selectively semipermeable microcapsules.

As mentioned above, the release rate of various components from the core of these microcapsules can be modified by the addition of solvents to the core. For example, adding a paraffinic oil (a very poor solvent for the shell wall) to the core will dramatically decrease the release of the core materials. The addition of a good solvent for the shell wall material will accelerate the release. The chemical nature and the amount of the core diluent used determines its effect on the release.

DETAILED DESCRIPTION OF SPECIFIC EMBODIMENTS

Figure 1:
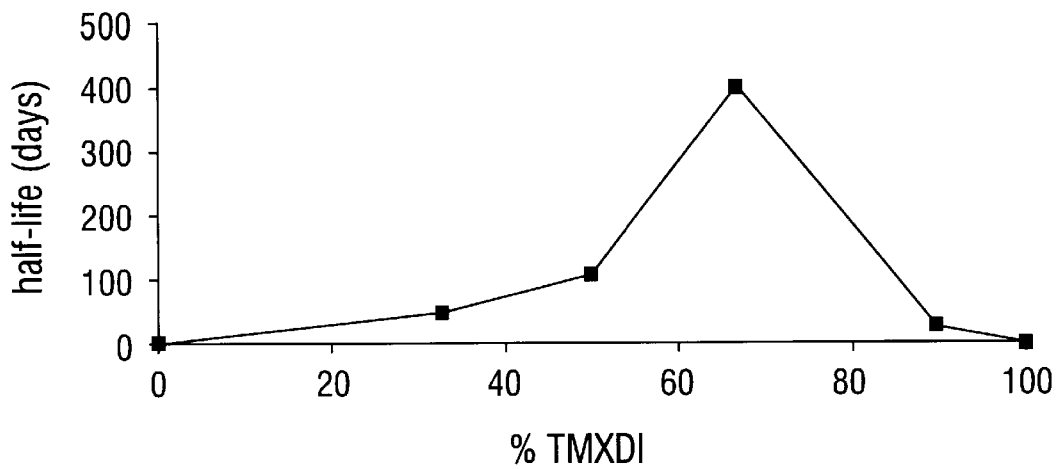
FIG. 1 is a graph of the core material release half life in days as a function of the percent isocyanate (NCO) equivalents from TMXDI (meta-tetramethylxylylene diisocyanate) in isocyanate blends containing TMXDI and Desmodur N3200 (the trifunctional biuret adduct of hexamethylene diisocyanate), where the amine used for curing was TETA (triethylene tetramine).

An encapsulation method has been discovered that produces mechanically strong microcapsules with readily adjustable release rates. The release is controlled by the capsule's shell wall without the need for microporosity or mechanical rupture. This is accomplished by manipulating the molecular composition of the shell wall, specifically by varying the relative amounts in a novel blend of aliphatic isocyanates. Specifically, it has been found that a two component blend containing a trifunctional adduct of a linear aliphatic isocyanate and a difunctional aliphatic isocyanate, which itself contains a cycloaliphatic ring or an aromatic ring segment, can be crosslinked interfacially by a polyamine (i.e., a polyfunctional amine) to produce a polyurea wall with a permeability that is proportional to the ratio of the difunctional ring-containing isocyanate to the trifunctional linear aliphatic isocyanate.

The encapsulating process can be conducted continuously or batchwise and preferably involves five steps:

1. The two isocyanates, the trifunctional adduct of a linear aliphatic isocyanate and the diisocyanate containing the ring segment, are mixed with the core material to make the internal phase (IP);
2. A protective colloid is dissolved in water to make the external phase (EP);
3. The internal phase is dispersed into the external phase to form a oil-in-water emulsion;
4. A polyamine is added to the emulsion; and
5. The mixture is heated at 40–60° C. until the isocyanate infrared absorption peak at 2270 cm$^{-1}$ disappears, usually taking about 0.5–3 hours.

An additional feature of this invention is that it provides a means of producing capsules through a single, continuous process wherein portions of the capsule population can be made with different release rates. In this way a capsule slurry can be made that provides optimum delivery rates timed for different periods of an application's lifecycle. With a herbicide for example, fast release for a strong initial effect, intermediate release to control regrowth, and long term release for full season control can be designed into one capsule slurry. This can easily be achieved by varying the relative amounts of the two isocyanates introduced into the stream of core material in step (1) through individual feed pumps in a programmed manner in-line and prior to the emulsification.

Trifunctional adducts of linear aliphatic isocyanates useful in this invention are the products of the reaction of a diisocyanate containing n methylene groups and a coupling reagent such as water or a low molecular triol like trimethyol propane, trimethyol ethane, glycerol, or hexanetriol. The starting diisocyanate suitably can have the formula:

$$O=C=N-(CH_2)_n-N=C=O \qquad (5)$$

where n is from about 4–18. Examples of suitable triisocyanates, where n=6, include the biuret containing adduct of hexamethylene-1,6-diisocyanate (6) (Desmodur N3200, from Miles; Tolonate HDB, from Rhone-Poulenc; Luxate HB3000 from Olin), triisocyanurate of hexamethylene-1,6-diisocyanate (7) (Desmodur N3300, from Miles; Tolonate HDT, from Rhone-Poulenc; Luxate HT2000 from Olin), and the triisocyanurate adduct of trimethylol propane and hexamethylene-1,6-diisocyanate (8). These compounds have the formulas:

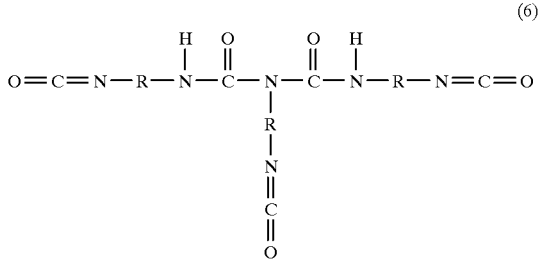

(6)

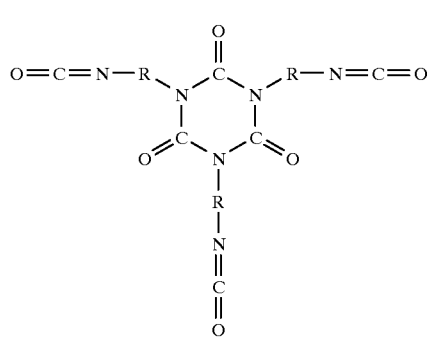

(7)

and

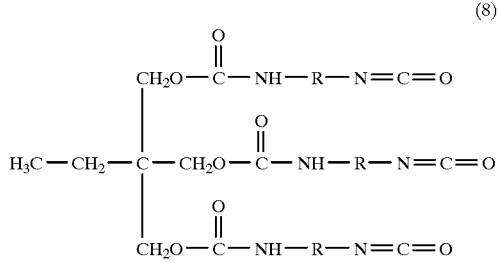

(8)

where R is —$(CH_2)_n$—, and n is 6 as mentioned above.

The aliphatic diisocyanates containing the cycloaliphatic or aromatic ring segments that are useful in this invention include meta-tetramethylxylylene diisocyanate (5), 4,4'-diisocyanato-dicyclohexyl methane (Desmodur W from Miles), and isophorone diisocyanate.

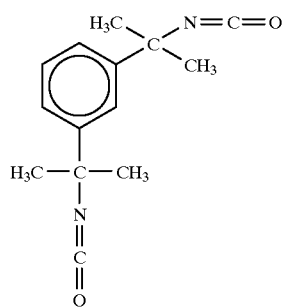

(9)

It should be understood that the above materials need not be 100% pure. For example, commercial grades of trifunctional isocyanates are described as having functionality between 2.6–3.4. The inclusion of some higher or lower molecular weight analogs with the trifuncational isocyanates, resulting in average functionality that is not exactly 3.0, is acceptable in the present invention.

The preferred polyamines are diethylene triamine and triethylene tetraamine, but other similar polyamines are also expected to function adequately. Examples of other suitable polyamines are iminobispropylamine, bis(hexamethylene) triamine, polyoxypropylenetriamines, amine epoxy adducts, and the alkyl diamines from ethylene diamine up to hexamethylene diamine (i.e., in which in which the alkyl group has from about 2–6 carbon atoms).

Protective colloids useful in this invention include gelatin, casein, polyvinyl alcohol, alkylated polyvinyl pyrrolidone polymers, maleic anhydride-methyl vinyl ether copolymers, styrene-maleic anhydride copolymers, maleic acid-butadiene and diisobutylene copolymers, sodium and calcium lignosulfonates, sulfonated naphthalene-formaldehyde condensates, modified starches, and modified cellulosics like hydroxyethyl or hydroxypropyl cellulose, and carboxymethyl cellulose.

Any water immiscible liquid, low melting solid (M.P.<80° C.), or oil solution of a water insoluble material can be encapsulated by this method. Agricultural pesticides are one suitable example. Herbicides, such as the acetanilides alachlor, acetochlor, and butachlor, are particularly preferred core materials. More than one herbicide could be included in the core of the same microcapsule.

Other agriculturally acceptable chemicals can also be included in the core, in addition to or in place of a herbicide. In one preferred embodiment, the core contains both a herbicide and a safener. The latter component protects one or more desired plants from the herbicidal effects of the former. This embodiment allows the herbicide to kill undesired plants while protecting desired plants. A variety of safeners are known in the herbicide field. When the herbicide included in the core is an acetanilide, suitable safeners would include Furilazole, AD67 (Nitrokemia; 1-oxa-4-azaspiro-4,5-decane, 4-dichloroacetyl) dichlormid, and benoxacor.

The core of the microcapsules can optionally contain one or more solvents, which can be selected to modify the release rate of the capsule contents. Suitable solvents include ones that are poor solvents for the shell wall, such as paraffinic oils having about 12–28 carbon atoms, and alkylated biphenyls or naphthalenes. Examples of such materials are Norpar 15, Exxsol D 110 and D130, Orchex 692 (all from Exxon Co.); Suresol 330 (from Koch); and diisopropyl naphthalene. Suitable solvents also include ones that are good solvents for the shell wall, such as highly aromatic solvents or esters like Aromatic 200 (Exxon), Citroflex A-4 (Pfizer), and diethyl adipate.

The compositions of the present invention can be prepared as liquid concentrates that contain a suspension or dispersion of the microcapsules. Such a liquid concentrate can be diluted with water and then applied to plants or soil by spraying, using spray equipment that is well known in the herbicide field. Alternatively, a composition of the present invention can take the form of a spray solution, suitable for spraying without further dilution.

The following examples are given to illustrate certain embodiments of the invention, but not to limit the overall scope of the invention.

EXAMPLES 1–11

External Phase (EP) Preparation:

A 16 ounce jar is charged with 285.5 g of hot water (60° C.). While stirring, 8.2 g of 188MT technical gelatin (from Milligan & Higgins, Johnstown, NY) is added. The gelatin dissolves in 10 to 20 minutes. The jar is then sealed and placed in a 50° C. oven until needed. For best results the solution should be used within 8 hours. In some of the examples below, 225A edible gelatin is substituted for the 188MT.

9

Internal Phase (IP) Preparation:

A 16 ounce jar is charged with 371.9 g of alachlor that has been preheated to 50° C. The two isocyanates are the weighed into the jar, 22.7 g of Desmodur N3200 (the trifunctional biuret adduct of hexamethylene diisocyanate) and 7.5 g m-TMXDI (meta-tetramethylxylylene diisocyanate). The solution is agitated to obtain a clear, homogeneous solution. The sealed jar is then placed in a 50° C. oven until needed. Again, for best results, the solution should be used within 8 hours.

Emulsification:

The EP is added to a commercial Waring blender cup that has been preheated to 50° C. The commercial Waring blender (Blender 700, Waring Products Division, Dynamics Corporation of America, New Hartford, Conn.) is powered through a 0–140 volt variable autotransformer. With the speed of the blender set by the transformer at 60 volts, the IP is added to the EP over a 16 second interval. Within 4 seconds the speed of the blender is increased by increasing the voltage to 110; this speed is maintained for 15 seconds (time=0). The emulsion is transferred to a one liter beaker on a hot plate and stirred.

Cure:

Within 3 minutes after emulsification, 6.8 g of TETA (triethylene tetramine) in 7 g water is added to the stirred emulsion. The beaker is covered and the temperature is maintained at 50° C. for 2 hours, or until the isocyanate infrared absorbance peak at 2270 cm$^{-1}$ disappears.

Formulation:

To the slurry, 20.5 g of a 2% aqueous solution of Proxel was added as a preservative. The capsule slurry may be formulated further in any number of ways. However for the purposes of analyzing the release rates of the capsules, the above slurry was simply divided equally into two portions: 346 g which contained no further modifications, labeled 1A (pH=7.86), and the other 346 g which was modified by the addition of 10 g NaCl and 20 g $CaCl_2$, labeled 1B (pH= 6.84). In this case, the salts improved the product's package stability by equalizing the densities of the capsules with the EP, and by reducing the solubility of the alachlor in the EP. The mean particle size was 3 microns. Examples 2 through 4 and comparative examples 5 and 6 were prepared by the same procedure. The only significant variant was the relative amounts of the two isocyanates. Examples 7 through 11 also followed the same procedure except DETA (diethylene triamine) was used as the polyamine, and acetochlor was the herbicide encapsulated. In Examples 7–11, the core also contained Furilazole, a safener. The compositions are given in Tables 1 and 2 below.

EXAMPLE 12

The preparation was the same as in Example 3 except 7.16 g DETA was used in place of the 7.61 g TETA. The Higuchi release half life of this capsule was determined as 152 years.

TABLE 1

| Description | Ingredient | Weights (grams) | | | | | |
|---|---|---|---|---|---|---|---|
| | | Example 1 | Example 2 | Example 3 | Example 4 | Example 5 | Example 6 |
| External Phase | | | | | | | |
| Water | Water | 285.5 | 284.7 | 284.7 | 284.7 | 285.4 | 284.7 |
| Protective Colloid | Gelatin | 8.2 | 5.8 | 8.2 | 5.8 | 8.2 | 5.8 |
| Internal Phase | | | | | | | |
| Core | Alachlor | 371.9 | 371.9 | 371.9 | 371.9 | 371.9 | 371.9 |
| Flexible triisocyanate | N3200 | 22.7 | 18.6 | 12.7 | 4.3 | 31 | 0 |
| Rigid diisocyanate Crosslinker | TMXDI | 7.5 | 12.2 | 16.9 | 25.8 | 0 | 28.6 |
| Polyamine | TETA | 6.8 | 7.3 | 7.6 | 8.6 | 5.9 | 8.6 |
| Water Compounding | | 7 | 9.3 | 7.9 | 8.9 | 7 | 8.9 |
| Preservative | 2% aq Proxel | 23.1 | 21.5 | 35.6 | 20 | 20.4 | 22.2 |
| Water | | 0 | 20 | 20 | 40 | 0 | 20 |
| Totals | | 732.7 | 751.3 | 765.5 | 770 | 729.8 | 750.7 |
| % wall on Core | | 10 | 10 | 10 | 10 | 10 | 10 |
| % of isocyanate equivalents | | | | | | | |
| from N3200 | | 67 | 50 | 33 | 10 | 100 | 0 |
| from TMXDI | | 33 | 50 | 67 | 90 | 0 | 100 |
| Higuchi Release Half Life | | 45 days | 130 days | 555 days | 29 days | 26 hours | 20 hours |

TABLE 2

| Description | Ingredient | Example 7 | Example 8 | Example 9 | Example 10 | Example 11 |
|---|---|---|---|---|---|---|
| External Phase | | | | | 5597324 | |
| Water | Water | 284.7 | 284.7 | 285.3 | 284.8 | 285.3 |
| Protective Colloid | Gelatin | 5.8 | 5.8 | 8.2 | 5.8 | 8.2 |
| Internal Phase | | | | | | |
| Core Active | Acetochlor | 360 | 360 | 360 | 360 | 360 |
| Safener | Furilazole | 12.1 | 12 | 12.1 | 12 | 12 |
| Flexible triisocyanate | N3200 | 22.7 | 18.3 | 15.1 | 12.7 | 29 |
| Rigid diisocyanate Crosslinker | TMXDI | 7.5 | 12.3 | 15.1 | 16.9 | 2.2 |
| Polyamine | DETA | 6.4 | 6.9 | 7.1 | 7.2 | 6.1 |
| Water Compounding | | 6.4 | 7.6 | 7.4 | 7.3 | 7.1 |
| Preservative | 2% aq Proxel | 22.8 | 19.9 | 20.1 | 21.4 | 21.1 |
| Water | | 0 | 0 | 0 | 0 | 0 |
| Totals | | 728.4 | 727.5 | 730.4 | 728.1 | 731 |
| % wall on Core | | 10 | 10 | 10 | 10 | 10 |
| % of isocyanate equivalents | | | | | | |
| from N3200 | | 67 | 50 | 40 | 33 | 90 |
| from TMXDI | | 33 | 50 | 60 | 67 | 10 |
| Higuchi Release Half Life | | 1 Year | 16 Years | 95 Years | 56 Years | 3 Days |

Release Rate Determination
Procedure:

Weigh 150 mg into 100 ml volumetric vessel, fill to mark with deionized water and mix. Transfer to ½ gal jar (rinsing 6× into jar), fill jar to a net weight of 1000 g with DI water or water plus buffer solution. Measure the pH of the slurry. (Nothing, including stirrer bars, should be added.) Sample at various times, filter through a 0.22 micron, 25 mm syringe filter (1) to a vial. The temperature was 28–30° C.

The percent of the core material released into a large volume of water, large enough to be treated as a perfect sink (i.e., no back diffusion), is plotted versus the square root of time. The plot is quite linear and its slope is the (Higuchi) rate constant for release. This constant is used to calculate the time required to release 50 percent of the capsules core, the release half life. The release half life for each Example is given in the above tables under the composition.

When the release half lives are plotted as a function of the percent isocyanate (NCO) equivalents from TMXDI in the N3200:TMXDI isocyanate blend, the release half life is seen to increase dramatically as the TMXDI content increases. (See FIG. 1.) A maximum occurs at the 67:33 (TMXDI:N3200) blend in isocyanate equivalents with TETA and at 60:40 with DETA as the crosslinker. Blends within the 10:90 to 70:30 ratio of equivalents, TMXDI to N3200, are the most preferred compositions. It is within this region that the segmental mobility of the shell wall, its permeability, is controlling the capsule's release rate. Solid state NMR relaxation studies indicate that the wall is homogeneous. Furthermore, the relaxation data indicates that the rigidity of the polymer on the high TMXDI side of the maximum is sufficient to render this region impermeable. The increasing release rate observed in this region, in contradiction to the NMR data, suggests the onset of microporosity. Incoherent film formation or excessive shrinkage could be the cause. Thus the 80:20 to 100:0 (TMXDI:N3200) region is not preferred for use.

Figure 2:
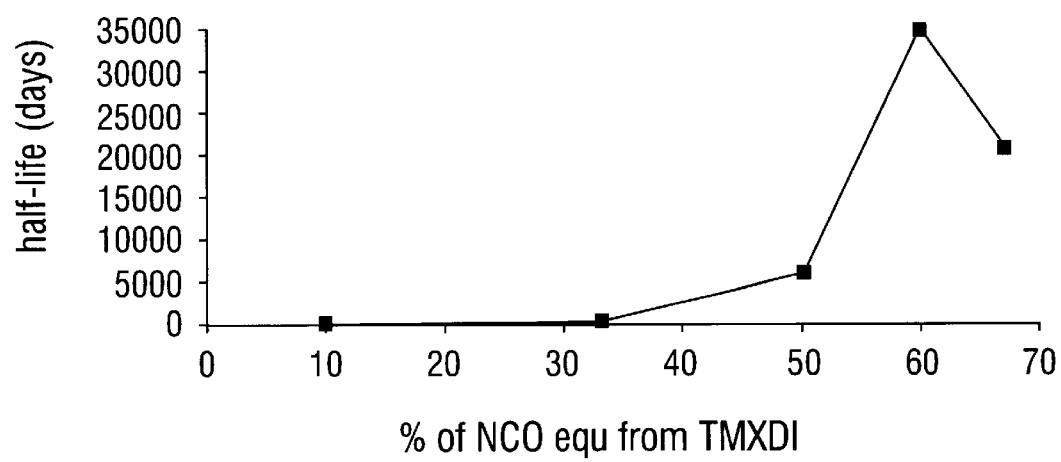
FIG. 2 is a graph of core material release half life as in FIG. 1, but for compositions where the amine used for curing was DETA.

FIG. 2 shows the release half lives for compositions where the amine was DETA instead of TETA.

EXAMPLE 13

EP Preparation:

A ½ gallon jar is charged with 1227.31 g of hot water (60° C.). While stirring, 35.35 g of 25OTG technical gelatin (from Milligan & Higgins, Johnstown, N.Y.) is added. The gelatin dissolves in 10 to 20 minutes. The jar is then sealed and placed in a 50° C. oven until needed. As before, for best results the solution should be used within 8 hours.

IP Preparation:

A ½ gallon jar is charged with 1600 g of a composition that contained 30 parts acetochlor plus 1 part Furilazole safener, the composition having been preheated to 50° C. The two isocyanates are the weighed into the jar; 78.69 g of Desmodur N3200 (the trifunctional biuret adduct of hexamethylene diisocyanate) and 25.84 g m-TDI (meta-tetramethylxylylene diisocyanate). The solution is agitated to obtain a clear, homogeneous solution. The sealed jar is then placed in a 50° C. oven until needed. Again, for best results, the solution should be used within 8 hours.

Emulsification:

The EP is added to a commercial (1 gallon) Waring blender cup (as described above) that has been preheated to 50° C. With the speed of the blender set at medium and the transformer at 60 volts, the IP is added to the EP over a 35 second interval. Within 5 seconds the speed of the blender is increased by changing blender setting to high and increasing the voltage to 110, this speed is maintained for 45 seconds (time=0). The emulsion is transferred to a four liter beaker on a hot plate and stirred.

Cure:

Within 3 minutes after emulsification, 23.47 g of TETA (triethylene tetramine) in 23.47 g water is added to the stirred emulsion. The beaker is covered and the temperature is maintained at 50° C. for 2 hours, at which time the isocyanate infrared absorbance peak at 2270 cm$^{-1}$ is essentially gone, i.e. 90+% converted.

Formulation:

To the slurry, 88.17 g of a 2% aqueous solution of Proxel was added as a preservative. The capsule slurry was modified further by the addition of 102.17 g NaCl and 204.35 g CaCl$_2$. The mean particle size was 3 microns. The wall is a blend of 33% (by equivalents) TMXDI and 67% Desmodur N3200 cured with TETA at an 8% wall to core ratio.

The wall to core ratio is calculated by adding the amount of triisocyanate, diisocyanate, and curing agent, and dividing that sum by the amount of active ingredients to be encapsulated (e.g., (78.69 g N3200+25.84 g TMXDI+23.47 g TETA)/(1600 g acetochlor and Furilazole)=8%).

The release rate was measured by the procedure described above, and the Higuchi release half life was determined to be 42 days ultimately (an expected value of 25 days was assigned initially based on representative formulas.

EXAMPLE 14

The above example was repeated, except the relative amount of TMXDI was reduced in the IP; 90.36 g of Desmodur N3200 and 15.07g m-TMXDI were used. In the cure, 22.57 g of TETA in 22.57 g of water was added to the emulsion. In all other respects, the preparation was identical to Example 13. The mean particle size was again 3 microns. The wall is a blend of 20% (by equivalents) TMXDI and 80% Desmodur N3200 cured with TETA at an 8% wall to core ratio. The release rate was measured, and the release half life was determined to be 3 days ultimately (an expected value of 5–7 days was assigned initially based on representative formulas).

EXAMPLE 15

Example 13 was repeated again, except no TMXDI was used in the IP; only 134.29 g of Desmodur N3200 was used. In the cure, 25.71 g of TETA in 25.71 g of water was added to the emulsion. In all other respects, the preparation was identical to Example 13. The mean particle size was 3 microns. The wall is 100% Desmodur N3200 cured with TETA at an 8% wall to core ratio. The Higuchi release half life was determined to be 4 hours ultimately (an expected value of 1 day was assigned initially based on representative formulas).

Bioefficacy Testing
Procedure for 14 Day Efficacy

A 14 day, wet/dry bioassay was performed on the above compositions to determine if the three different release rates would translate into three different efficacies. Rox orange sorghum and barnyardgrass were seeded ½ inch deep into the standard 4 inch square plots which contained a Dupo silt loam soil mix. All herbicides were applied by a track sprayer in 20 gallons of liquid per acre spray volume. The rates of acetochlor application were from 0.032–1.0 lb/acre ai. Treatments were made to two soil moisture regimes, wet and dry. Wet soil conditions consisted of making spray applications to slightly moist soil and maintaining most soil conditions for the duration of the test. Dry soil conditions consisted of spray applications made to air-dried soil which would be maintained dry for the first 24 hours after application, after which all pots would be watered and maintained moist for the duration of the test. All pots were placed in a warm supplemental lighted greenhouse and alternately subirrigated and overhead misted as necessary to maintain adequate moisture for the duration of the test. Two weeks after application the herbicidal efficacy was rated.
Results The efficacy was found to be directly related to release half life. The composition of Example 13 with 33% TMXDI gave 65% weed inhibition (average across rates) within the 14 day test period, indicating a low release rate. The composition of Example 14 with 20% TMXDI provided 75% control (average across rates), and Example 15 with no TMXDI yielded 84% control (average across rates). As the TMXDI content is decreased, the release rate and thus the initial bioefficacy increases. The slower initial release rate should allow the high TMXDI formulas to last longer— providing longer weed control—before their cores are exhausted. The length of control was determined in the following test.

Procedure for Controlled Release Greenhouse Test— length of control.

A controlled release (CR) greenhouse test was conducted with the compositions of Examples 13 and 14, using Harness® EC herbicide (Monsanto) as the control. Green foxtail was seeded ½ inch deep into standard 4 inch square pots which contained a Dupo silt loam soil mix. All herbicides were applied at two rates, 0.25 lb/a and 0.5 lb/a (ai) by a track sprayer (20 gal/acre) as before. Two ply cheese cloth (or nylon screening) was placed ½ inch below the treated soil surface to enable removal of the top ½ inch of soil surface to allow planting at subsequent bioassay dates. After planting the cheese cloth was removed and discarded. The weeds were planted every 7 days and evaluated 2 weeks later. The soil covers were lightly crumbled or broken up and replaced again over the newly seeded pots. The test ran 60–70 days with seven plantings and evaluations.
Results Harness EC showed the highest levels of control initially with >90% green foxtail efficacy at 0, 7, and 14 days. However, after eighteen days from application, the two controlled release examples (13 and 14) began to show superior green foxtail efficacy. These CR formulations maintained their superiority over Harness EC throughout the remainder of the thirty day bioassay period. At the higher application rate, the composition of Example 13 provided more control at 30 days than did Example 14, consistent with release half life and TMXDI content.

EXAMPLE 16

EP Preparation:

A ½ gallon jar is charged with 1215.16 g of hot water (60° C.). Then 50.67 g of Sokalan CP9 (from BASF, Parsippany, N.J.) and 1.26 g of casein are added. The casein dissolves in 20 to 30 minutes with stirring, after which the pH is adjusted down to 7.7 with 0.85 g of citric acid monohydrate. The jar is then sealed and placed in a 50° C. oven until needed. For best results the solution should be used within 24 hours.

IP Preparation:

A ½ gallon jar is charged with 1600 g of a composition that contained 30 parts acetochlor plus 1 part Furilazole safener, the composition having been preheated to 50° C. As in Example 13, the two isocyanates are then weighed into the jar; 78.69 g of Desmodur N3200 and 25.84 g m-TMXDI. The solution is agitated to obtain a clear, homogeneous solution. The sealed jar is then placed in a 50° C. oven until needed. The solution should be used within 8 hours.

Emulsification:

The EP is added to a commercial (1 gallon) Waring blender cup, as described above, that has been preheated to 50° C. With the speed of the blender set at medium and the transformer at 60 volts, the IP is added to the EP over a 35 second interval. Within 5 seconds the speed of the blender is increased by increasing the voltage to 100, this speed is maintained for 45 seconds (time=0). The emulsion is transferred to a four liter beaker on a hot plate and stirred.

Cure:

Within 3 minutes after emulsification, 23.47 g of TETA (triethylene tetraamine) in 23.47 g water is added to the stirred emulsion. The beaker is covered and the temperature is maintained at 50° C. for 2 hours, at which time the isocyanate infrared absorbance peak at 2270 cm$^{-1}$ is essentially gone, i.e. 90+% converted.

Formulation:

To the slurry, 88.17 g of a 2% aqueous solution of Proxel and 1.17g of Kelzan (from Kelco, San Diego, Calif.) was added as preservative and thickener. The formulation was completed with the addition of 90.9 g of a Sokalan CP9 solution that had been diluted to 1.4% solids with water. The mean particle size was 2.7 microns. The wall is a blend of 33% (by equivalents) TMXDI and 67% Desmodur N3200 cured with TETA at an 8% wall to core ratio. The release rate was measured by the above procedure, and the Higuchi release half life was determined to be 77 days, ultimately.

EXAMPLE 17

The above example was repeated, except the relative amount of TMXDI was reduced in the IP; 90.36 g of Desmodur N3200 and 15.07g m-TMXDI was used. In the cure, 22.58 g of TETA in 22.58 g of water was added to the emulsion. In all other respects, the preparation was identical to Example 16. The mean particle size was again 2.7 microns. The wall is a blend of 20% (by equivalents) TMXDI and 80% Desmodur N3200 cured with TETA at an 8% wall to core ratio. The release rate was measured, and the Higuchi release half life was ultimately determined to be 34 days.

EXAMPLE 18

Example 16 was repeated, except the relative amount of TMXDI was increased in the IP; 73.94 g of Desmodur N3200 and 30.21g m-TMXDI were used. In the cure, 23.85 g of TETA in 23.85 g of water was added to the emulsion. In all other respects, the preparation was identical to Example 16. The mean particle size was again 2.7 microns. The wall is a blend of 38% (by equivalents) TMXDI and 62% Desmodur N3200 cured with TETA at an 8% wall to core ratio. The Higuchi release half life was ultimately determined to be 254 days.

COMPARATIVE EXAMPLE 1

Acetochlor can be encapsulated using the techniques disclosed in U.S. Pat. No. 4,280,833, using PAPI 2027 (polymethylene-polyphenylisocyanate from Union Carbide) and hexamethylene diamine to make the shellwall. A single speed Waring blender is connected to a variable transformer. Into the blender cup, 270.2 g of water and 20.31 g of REAX 88B (a 40% sodium lignosulfonate solution from Westvaco), both at 50° C., are added. In a separate bottle, 12.4 g Furilazole is dissolved into 359.5 g of hot (50° C.) acetochlor. To this acetochlor:safener (30:1) solution, 26.4 g of PAPI 2027 are added and dissolved.

With the transformer at 25 acV, the PAPI/acetochlor solution is added to the blender cup within 4 to 5 second period. The blender speed is increased from 25 to 85 over this 4–5 second period. After the blender contents have mixed at high shear for 30 seconds, add 25.9 g of a 43.5% solution of hexamethylene diamine (HMD) rapidly to the vortex. Precisely 5 seconds after the HMD addition is complete, decrease the transformer to 30. Maintain the mix at this low shear for 30 minutes.

Formulation: To the above slurry, add 37.5 g of NaCl within 2 seconds. After 30 seconds, add 37.5 g of CaCl$_2$ over a 15 minute period. The product is mixed for an additional 15 minutes, after which, the 41.6 g of Kelzan S/Proxel premix is added, consisting of 0.42 g Proxel and 0.42 g Kelzan in 40.74 g water. The particle size is 4.5 microns. The release rate into water occurs in two stages; the first, initial stage sees 12% of the acetochlor released such that the Higuchi half life is 342 days, followed by a second, very slow release stage with a Higuchi half life of 13 years. This product's performance is poorly simulated by release through the shellwall, which would predict little to no bioefficacy. It does exhibit some bioefficacy in the field, and this contradiction has led to the proposal that it releases as a result of a rupture mechanism initiated by environmental stresses.

COMPARATIVE EXAMPLE 2

A commercial sample of Topnotch, sold by Zeneca, and described in the literature as microencapsulated acetochlor made using aromatic isocyanates (U.S. Pat. No. 4,643,764); polymethylene-polyphenylisocyanate (PAPI) and toluenediisocyanate (TDI). These isocyanates are partially hydrolyzed to amines at the droplet interface, which in turn, react with unhydrolyzed isocyanate to form the shellwall. The exact composition, however, is proprietary and unknown. The release into water (30° C.) is complete, 100% of the acetochlor is released within 24 hours.

Diffusion Model Release Rates

Examples 16, 17, and 18 were also analyzed using the solutions derived by S. Omi, et al. for the case of diffusion of small molecules through a spherical shell. In this model, a plot of the log of the fraction of active remaining in the microcapsule versus time is linear. Specifically, Fraction of active remaining in capsule at time t=$(C_{L\infty}-C_L)/(C_{L\infty}-C_{L0})=\exp\{-6Dt/(r_0^2 -r_i^2)\}$, or $-\ln[(C_{L\infty}-C_L)/(C_{L\infty}-C_{L0})]=6Dt/(r_0^2 -r_i^2)\}$, where $C_L$, $C_{L\infty}$, and $C_{L0}$=concentration outside the capsule at time t, at t=∞, and t=0, D=the diffusion coefficient of the core material through the wall, and $r_0$, $r_i$=the outer and inner radii of the capsule shell.

Figure 3:
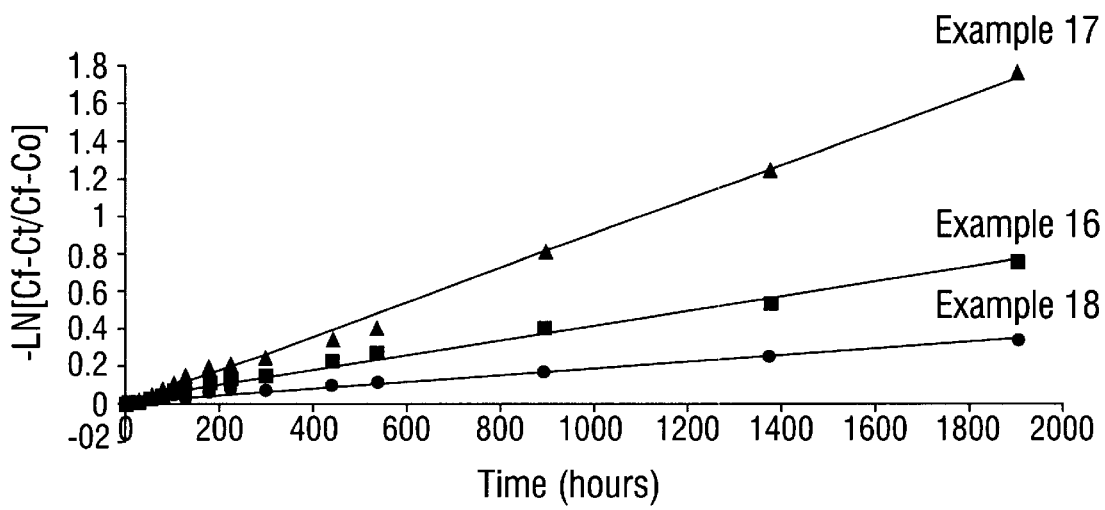
FIG. 3 is a graph of the natural log of the fraction of active ingredient remaining in the core of microcapsules as a function of time for the compositions of Examples 16, 17, and 18.
Figure 4:
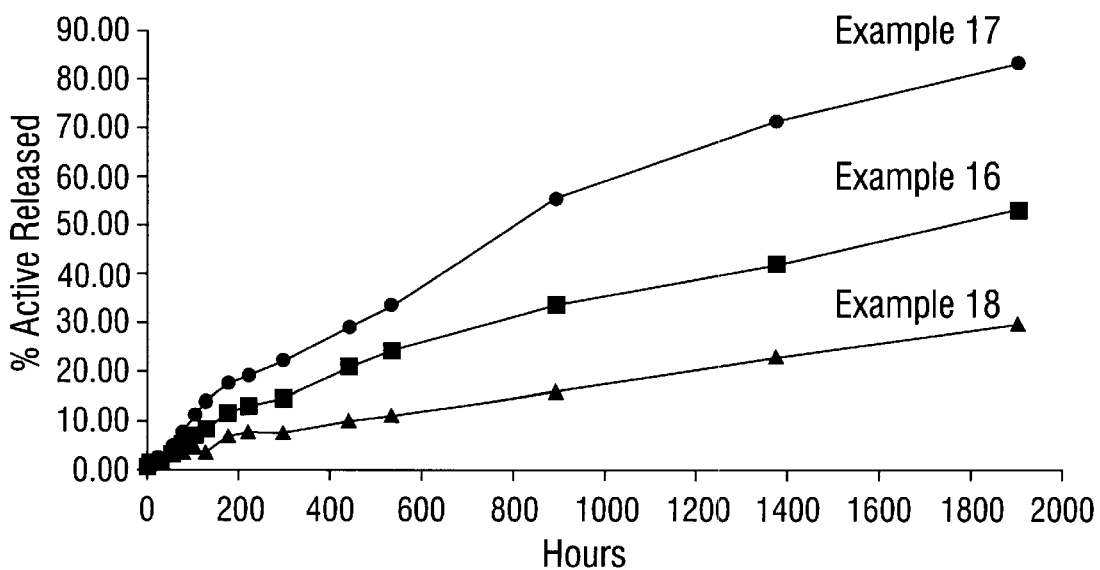
FIG. 4 is a graph of the percentage of acetochlor released from the core of microcapsules as a function of time.

This linear relationship was indeed found to be the case for these examples. (See FIG. 3.) The Diffusion Model half lives for Examples 16, 17, and 18 are 74 days, 32 days, and 165 days respectively, and are a function of the TMXDI concentration in the isocyanate blend. This model deviates from the Higuchi values as the release rates decrease, and as the total amount of core released increases. (See FIG. 4.) The diffusion model gives a better fit out to 90% released, and, as such, is believed to yield a better prediction of length of control.

Bioefficacy Results for Controlled Release Greenhouse Test—Length of Control

Figure 5:
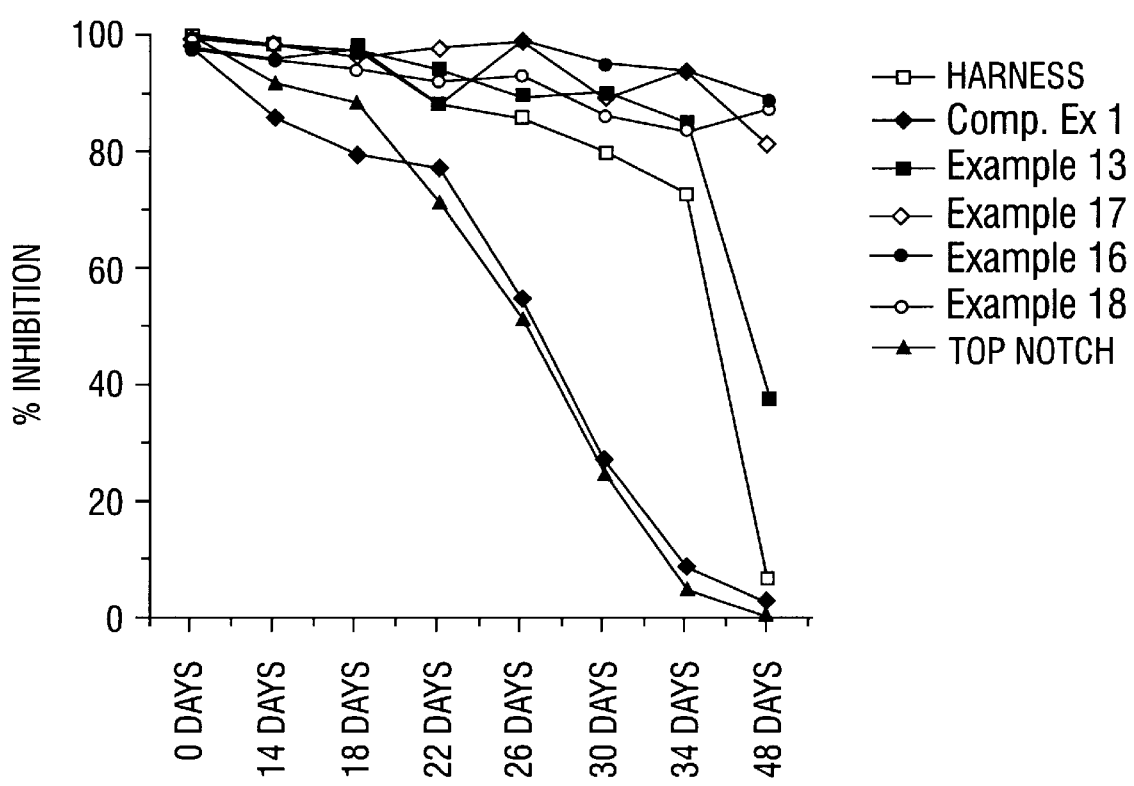
FIG. 5 is a graph of the herbicidal inhibition of several acetochlor formulations as a function of time.

A controlled release (CR) greenhouse test was performed, using generally the same procedure described above, except in some instances barnyardgrass was used in place of foxtail. Nylon screening was used instead of cheese cloth. The compositions of Examples 16, 17, and 18 along with Harness EC showed high levels of weed control with >85% barnyardgrass efficacy and >90% green foxtail efficacy at 0, 7, 14, 18, and 22 days. After thirty days from application the Harness EC began to show significantly reduced efficacy compared to the examples. The CR formulas of the examples maintained their superiority over Harness EC throughout the remainder of the 3448 day bioassay period. The compositions of Comparative Example 1 and Comparative Example 2 (Topnotch), did not extend the length of weed control under these same conditions. (See FIG. 5.)

Field Trials

The compositions of Examples 16, 17, and 18 were also tested in the field. These formulations improved the length-of-control residual activity of acetochlor. The relative differences in field performance were also analogous to the differences in the release half life and TMXDI content. Example 17 provided 80% control for 48 days and dropped to 40% control at 80 days; Example 16 provided 80% control for 54 days and dropped to 40% control at 80 days; and Example 18 provided 80% control for 62 days and dropped to 60% control at 80 days. As a comparison, the Harness EC (unencapsulated acetochlor) application dropped to 30% control at 80 days.

The core of the capsule may contain a diluent which can be used to modify the release profile. In Examples 19 through 23, a hydrophobic, poor solvency diluent is added to the core to reduce the amount of herbicide in the microcapsule at the later stages of the release profile. The last few percentages of core material are usually released very slowly due to shellwall surface effects. Since the hydrophobic, poor solvency diluent is retained in the microcapsule, it functions as a sacrificial replacement for what would otherwise be trapped herbicide.

EXAMPLE 19

EP Preparation:

A ½ gallon jar is charged with 1216.54 g of hot water (60° C.). Then 56 g of Sokalan CP9 (from BASF, Parsipanny, N.J.) and 1.85 g of casein are added. The casein dissolves in 20 to 30 minutes with stirring, after which the pH is adjusted down to 7.7 with 0.85 g of citric acid monohydrate. The jar is then sealed and placed in a 50° C. oven until needed. For best results the solution should be used within 24 hours.

IP Preparation:

A ½ gallon jar is charged with 1456.4 g of acetochlor technical (95.4%) preheated to 50° C. Then, 23.65 g of Furilazole safener (98%) are added and stirred until dissolved. This represents a 60:1 acetochlor:safener ratio in the core solution. To this homogeneous solution, 120 g of Norpar 15 are added. The two isocyanates are then weighed into the jar; 87.76 g of Desmodur N3200 and 17.48 g m-TMXDI. The solution is agitated to obtain a clear, homogeneous solution. The sealed jar is then placed in a 50° C. oven until needed. The solution should be used within 8 hours. The isocyanate composition is a blend of 77% (by equivalents) N3200 and 23% TMXDI.

Emulsification:

The EP is added to a commercial (1 gallon) Waring blender cup that has been preheated to 50° C. The commercial Waring blender (Waring Products Division, Dynamics Corporation of America, New Hartford, Conn., Blender 700) is powered through a 0–140 volt variable autotransformer. With the speed of the blender set at medium and the transformer at 60 volts, the IP is added to the EP over a 35-second interval. Within 5 seconds the speed of the blender is increased by increasing the voltage to 100, this speed is maintained for 45 seconds (time=0). The emulsion is transferred to a four liter beaker on a hot plate and stirred.

Cure:

Within 3 minutes after emulsification, 24.22 g of TETA (triethylene tetramine) in 21.32 g water is added to the stirred emulsion. The beaker is covered and the temperature is maintained at 50° C. for 2 hours, at which time the isocyanate infrared absorbance peak at 2270 cm$^{-1}$ is essentially gone.

Formulation:

To the slurry, 30.3 g of glycerol, 165.3 g of Irgasol DA liquid (a 40% solution of a sodium salt of a naphthalene sulfonate formaldehyde condensate from Ciba-Geigy), 15.07 g of Lattice NTC61 (a microcrystalline cellulose from FMC), 37.5 g of a 4.7% aqueous solution of Proxel, and 1.18 g of Kelzan K8C241 (from Kelco, San Diego, Calif.) were added. After allowing thirty minutes to dissolve the Kelzan, the formulation was completed with the addition of 32.98 g of disodium phosphate (anhydrous). The median particle size was 2.2 microns. The wall is a blend of 23% (by equivalents) TMXDI and 77% Desmodur N3200 cured with TETA at an 8% wall to core ratio.

EXAMPLE 20

EP Preparation:

A ½ gallon jar is charged with 1113.96 g of hot water (60° C.). Then 57.5 g of Sokalan CP9 and 1.9 g of casein are added. The casein dissolves in 20 to 30 minutes with stirring, after which the pH is adjusted down to 7.5 with 0.85 g of citric acid monohydrate. Then 127.3 g of glycerol are added. The jar is then sealed and placed in a 50° C. oven until needed. For best results the solution should be used within 24 hours.

IP Preparation:

A ½ gallon jar is charged with 1456.4 g of acetochlor technical (95.4%) preheated to 50° C. Then, 23.65 g of Furilazole safener (98%) are added and stirred until dissolved. Again this represents a 60:1 acetochlor:safener ratio in the core solution. To this homogeneous solution, 120 g of Norpar 15 are added. The two isocyanates are then weighed into the jar; 78.70 g of Desmodur N3200 and 25.84 g m-TMXDI. The solution is agitated to obtain a clear, homogeneous solution. The sealed jar is then placed in a 50° C. oven until needed. The solution should be used within 8 hours. The isocyanate composition is a blend of 67% (by equivalents) N3200 and 33% TMXDI.

Emulsification is accomplished in the manner specified in Example 19.

Cure:

Within 3 minutes after emulsification, 24.96 g of TETA in 21.97 g water is added to the stirred emulsion. The beaker is covered and the temperature is maintained at 50° C. for 2 hours, at which time the isocyanate infrared absorbance peak at 2270 cm$^{-1}$ is essentially gone.

Formulation:

To the slurry, 125.6 g of Irgasol DA liquid, 86.87 g of a 2% aqueous solution of Proxel, and 1.16g of Kelzan S (from Kelco, San Diego, Calif.) were added. After allowing thirty minutes to dissolve the Kelzan, the formulation was completed with the addition of 30.26 g of disodium phosphate (anhydrous). The median particle size was 2.4 microns. The wall is a blend of 33% (by equivalents) TMXDI and 67% Desmodur N3200 cured with TETA at an 8% wall to core ratio.

Example 21

EP Preparation:

A ½ gallon jar is charged with 1216.54 g of hot water (60° C.). Then 56 g of Sokalan CP9 and 1.85 g of casein are added. The casein dissolves in 20 to 30 minutes with stirring, after which the pH is adjusted down to 7.7 with 0.85 g of citric acid monohydrate. The jar is then sealed and placed in a 50° C. oven until needed. For best results the solution should be used within 24 hours.

IP Preparation:

A ½ gallon jar is charged with 1456.4 g of acetochlor technical (95.4%) preheated to 50° C. Then, 23.65 g of Furilazole safener (98%) are added and stirred until dissolved. Again this represents a 60:1 acetochlor:safener ratio in the core solution. To this homogeneous solution, 120 g of Norpar 15 are added. The two isocyanates are then weighed into the jar; 78.70 g of Desmodur N3200 and 25.84 g m-TMXDI. The solution is agitated to obtain a clear, homogeneous solution. The sealed jar is then placed in a 50° C. oven until needed. The solution should be used within 8 hours. The isocyanate composition is a blend of 67% (by equivalents) N3200 and 33% TMXDI.

Emulsification is accomplished in the manner specified in Example 19.

Cure:

Within 3 minutes after emulsification, 24.96 g of TETA in 21.97 g water is added to the stirred emulsion. The beaker is covered and the temperature is maintained at 50° C. for 2 hours, at which time the isocyanate infrared absorbance peak at 2270 cm⁻is essentially gone.

Formulation:

To the slurry, 30.5 g of glycerol, 152.5 g of Irgasol DA liquid, 1.52 g of CMC-7L (carboxymethyl cellulose from Aqualon), 1.74 g of 100% Proxel GXL, and 1.16 g of Kelzan K8C241 were added. After allowing thirty minutes to dissolve the Kelzan, the formulation was completed with the addition of 61 g of disodium phosphate (anhydrous). The median particle size was 2.2 microns. The wall is a blend of 33% (by equivalents) TMXDI and 67% Desmodur N3200 cured with TETA at an 8% wall to core ratio.

Dynamic Release Rate Determination and Temperature Dependence

Release rates into water were determined for the compositions of Examples 19–21 under dynamic conditions. This required a modification in the procedure described above for the determination of release rates. Instead of sealed jars, the 150 to 200 mg samples of the test formulas were added to the release media in 1 liter dissolution vessels, covered, and stirred with a paddle type agitator revolving at 150 to 200 rpms. The vessels were submerged in a bath whose temperature could be controlled to within 1 ° C. in the 5 to 50° C. range. This modification resulted in faster release values compared to the more static determinations made above at the same temperature. The half lives under the dynamic conditions were about 50% shorter than those obtained on the same formulas under static conditions. These latter values are still useful as a relative measures of release rates, and can differentiate between formulas. However, the shorter half lives obtained under dynamic conditions are more realistic in the absolute sense, in that the length of control they predict is more closely in line with the greenhouse and field test results. Additionally, the temperature baths allow one to determine the temperature dependence of the release.

At 30° C., the release half life of Example 19 (23:77 TMXDI:N3200 shellwall) under this procedure and analyzed using the Diffusion Model was determined to be 30 days. This half life is referred to as the Dynamic Diffusion Model Half Life or DDM $t_{1/2}$. The DDM t $t_{1/2}$ for Example 21 (33:67 TMDXI:N3200 shellwall) was determined to be 73 days. Again the release is seen to be a function of the shellwall composition, with increasing amounts of TMXDI decreasing the rate of release. Example 20 had a DDM $t_{1/2}$ of 93 days, and reflects the effect of the presence of glycerol during the shellwall reaction.

Figure 6:
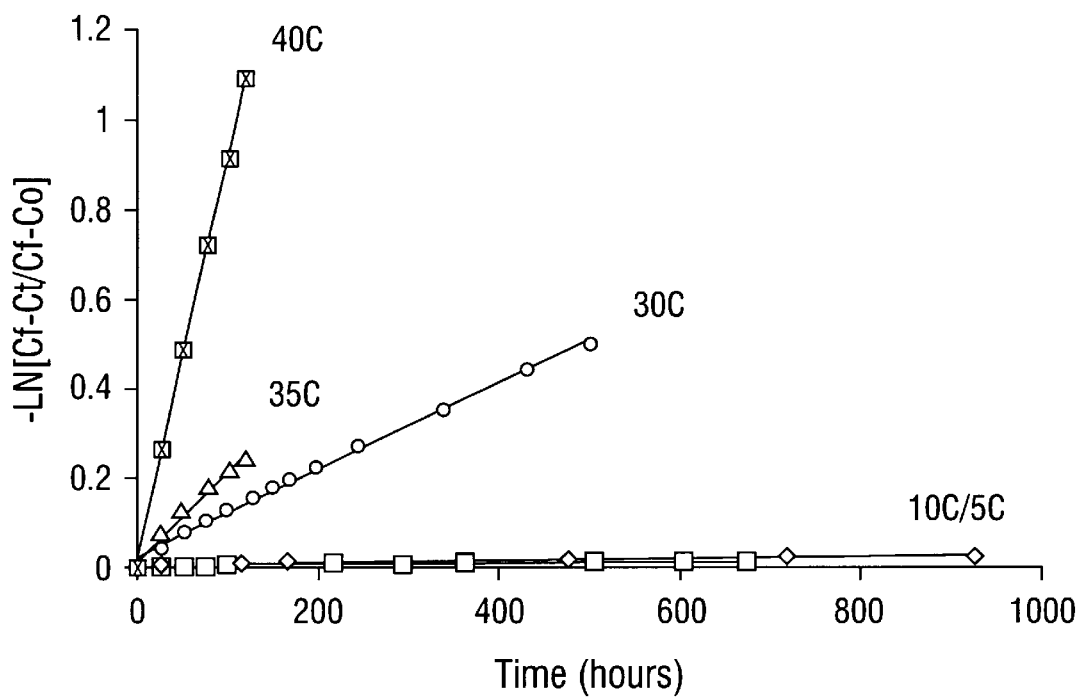
FIG. 6 is a graph of the natural log of the fraction of acetochlor remaining in microcapsules as a function of time, at several temperatures.

To illustrate the difference between the shellwalls disclosed above and the prior art microcapsules, the release test was performed with Example 21 and Comparative Example 1 at several temperatures. The results are summarized below. The graph (FIG. 6) is a visual confirmation of the excellent fit of the release data to the Diffusion Model. The release from the microcapsules of this invention responds to temperature in a manner consistent with a "diffusion through the shellwall" mechanism. Diffusion is accelerated by temperature in an exponential manner as is the release from Example 21. This response to temperature has favorable implications for the product's bioefficacy. Its release rate will increase with temperature in parallel to the increase in weed pressure that also follows temperature. The temperature dependence is also advantageous for early preplant or fall applications, wherein the capsules would lie dormant at cold temperatures until needed in the warm conditions of spring. The Comparative Example 1 on the other hand again failed to respond to temperature and the diffusion model.

TABLE 3

| Temperature (° C.) | Example 21 DDM $t_{1/2}$ (Half Life in Days) | Comparative Example 1 DDM $t_{1/2}$ Initial Stage - First 12% |
|---|---|---|
| 5 | 3292 | |
| 10 | 1181 | |
| 30 | 73 | 99 days (12% release), then 464 days for remainder, second stage |
| 35 | 14.5 | 70 days (12% release) |
| 40 | 3.25 | 72 days (12% release) |
| 45 | 0.96 | 63 days (12% release) |
| 50 | 0.55 | 59 days (12% release) |

Selective Diffusion

Figure 7:
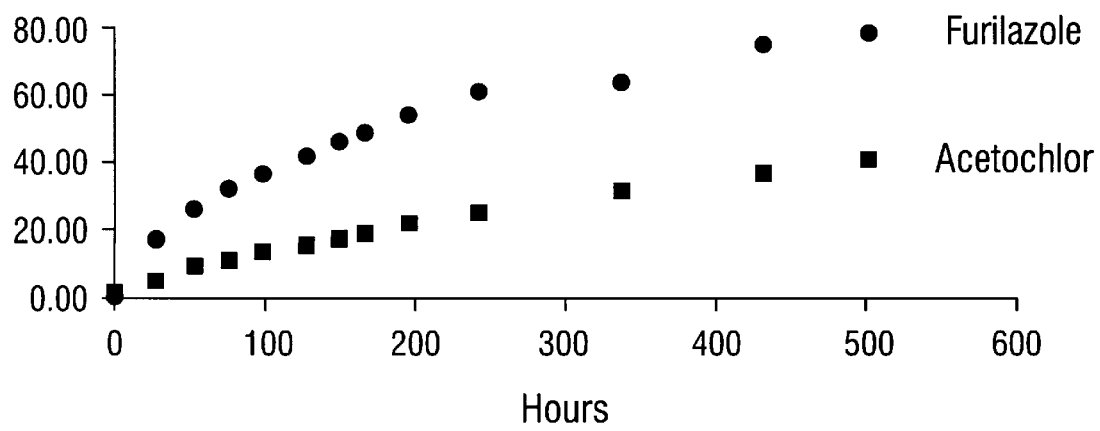
FIG. 7 is a graph of the percentage of Furilazole safener and acetochlor released from the core of a microcapsule as a function of time.
Figure 8:
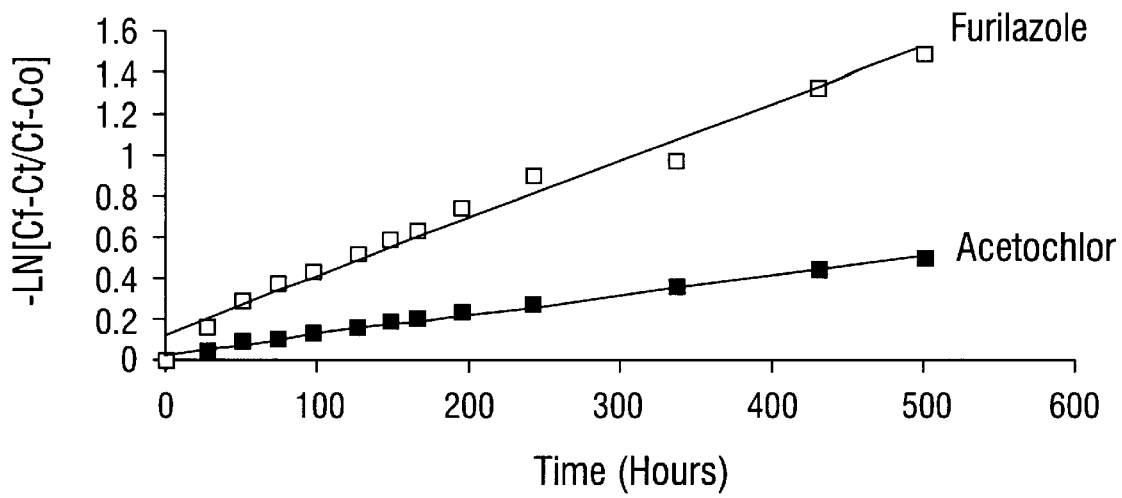
FIG. 8 is a graph of the natural log of the fraction of acetochlor and safener remaining in microcapsules as a function of time.

In addition to the favorable temperature dependence, the release rate is also dependent on the chemical nature of the permeant. Therefore, when the core of the microcapsule contains multiple components, they will diffuse out of the capsule at different rates. This property can be utilized to increase the safety of herbicides by incorporating a safener within the capsule that is more permeating, i.e., a safener that is more soluble in the shellwall or smaller in size than the herbicide. The release profiles of Example 19, results given below, were analyzed for the release of acetochlor and safener. The DDM $t_{1/2}$ of the safener (Furilazole) in Example 19 was determined to be 10 days, while DDM $t_{1/2}$ of 30 days was obtained for acetochlor. (See FIGS. 7 and 8.) Even though the acetochlor to safener ratio is about 60 to 1 inside the capsule, the difference in the rates of release produced an acetochlor:safener ratio of about 20 to 1 outside the microcapsule, in the release medium samplings. With acetochlor, Furilazole, and the microcapsules of this invention, the safener ratio outside the microcapsule is three times richer in safener than that inside the capsule, until the safener is exhausted. In a similar test performed on Comparative Example 1, the safener ratio outside the capsule was the same as the ratio inside the microcapsule, indicating the release is not selective in this prior art microcapsule.

The acetochlor to safener ratio in the core of the microcapsules used in the tests reflected in Table 4 was 57.14. The experiment was conducted at 30° C.

TABLE 4

| ppm | % | Av. | Std. | % | Available Aceto/ |
|---|---|---|---|---|---|

| Time (hrs) | Sqrt Time | Active (Acetochlor) | Std. Dev. | Acetochlor Released | Cf-Ct/ Cf-Co | ppm Furilazole | Dev. Furilazole | Safener Released | Safener Ratio |
|---|---|---|---|---|---|---|---|---|---|
| 0 | 0.00 | 0.30 | NA | 0.38 | 1.00 | 0.02 | 0.000 | 0.00 | 0.00 |
| 26.5 | 5.15 | 3.50 | 0.21 | 4.47 | 0.96 | 0.22 | 0.008 | 16.09 | 15.89 |
| 51.5 | 7.18 | 6.33 | 0.21 | 8.09 | 0.92 | 0.35 | 0.013 | 25.65 | 18.03 |
| 75.3 | 8.68 | 8.13 | 0.27 | 10.39 | 0.90 | 0.43 | 0.029 | 31.77 | 18.69 |
| 97.4 | 9.87 | 9.89 | 0.33 | 12.64 | 0.88 | 0.49 | 0.003 | 35.98 | 20.08 |
| 126.9 | 11.26 | 11.66 | 0.36 | 14.91 | 0.85 | 0.57 | 0.014 | 41.31 | 20.62 |
| 147.8 | 12.16 | 13.14 | 0.28 | 16.80 | 0.84 | 0.62 | 0.005 | 45.25 | 21.21 |
| 166.7 | 12.91 | 14.31 | 0.07 | 18.30 | 0.82 | 0.65 | 0.046 | 47.66 | 21.93 |
| 196.6 | 14.02 | 16.02 | 0.16 | 20.48 | 0.80 | 0.73 | 0.006 | 53.42 | 21.91 |
| 242.8 | 15.58 | 19.00 | 0.08 | 24.29 | 0.76 | 0.82 | 0.003 | 59.97 | 23.14 |
| 338.3 | 18.39 | 23.60 | 0.03 | 30.17 | 0.70 | 0.86 | 0.001 | 62.58 | 27.55 |
| 431.4 | 20.77 | 28.27 | 0.23 | 36.14 | 0.64 | 1.01 | 0.003 | 74.02 | 27.90 |
| 502.8 | 22.42 | 31.14 | 0.12 | 39.81 | 0.60 | 1.07 | 0.031 | 77.88 | 29.21 |
| Totals | | 78.22 | Calc | | | 1.3689 | Calc | | |

Crop Safety Testing

Two Dekalb corn hybrids, DK623 and DK634, with known acetanilide sensitivity were treated with the composition of Example 20 (CR 108A), a safened acetochlor EC with 30:1 acetochlor:Furilazole safener ratio, and the composition of Comparative Example 1. The experiment was conducted in a cool greenhouse (70/60° F.), and the pans containing the crop were irrigated by wet/dry cycling.

The percent of acetanilide injury caused by Example 20 is significantly less than that seen with either the unencapsulated Emulsion Concentrate of acetochlor containing twice the same safener, Furilazole; or with Comparative Example 1, the acetochlor encapsulated according to the prior art also containing twice the safener. The microcapsules of this invention allow one to use lower amounts of chemical safener and still increase the level of crop safety. This benefit is the result of controlled release during plant development that keeps the available, active concentration below levels toxic to the crop, and of the selective, faster release of safener early when it is most needed to protect the crop during the initial stages of development.

TABLE 5

%, Percent Acetanilide Injury, 13 days after treatment

| Formula | DK623, with 4 lb/acre a.i. | DK634, with 1 lb/acre a.i. | DK634, with 4 lb/acre a.i. |
|---|---|---|---|
| Example 20 | 3 | 3 | 17 |
| Acetochlor EC | 7 | 27 | 60 |
| Comparative Example 1 | 10 | 30 | 93 | a.i. = active ingredient, namely, acetochlor

The release and length of control can be affected by the nature of the diluent. Example 22 demonstrates this characteristic. Additionally, as in Example 23, the microencapsulated acetochlor formulations can be spiked with free acetochlor. This spiking can be used to obtain the strong initial weed control characteristic of an EC, and still achieve increased longevity from the encapsulated acetochlor.

EXAMPLE 22

The formula is made exactly as in Example 19 except that the Norpar 15 is replaced by Exxsol D130. The median particle obtained was 3 microns. The DDM $t_{1/2}$ of this microcapsule was determined to be about 377 days at 30° C. The rate of release, after taking the size difference into account, is only one fifth that seen in Example 19. The formula of this example is identified as 7253 in FIG. 9.

EXAMPLE 23

EP Preparation

A 1 quart jar is charged with 326.4 g of hot water (60° C.). Then 15 g of Sokalan CP9 and 0.5 g of casein are added. The casein dissolves in 20 to 30 minutes with stirring, after which the pH is adjusted down to 7.6 with 0.23 g of citric acid monohydrate. The jar is then sealed and placed in a 50° C. oven until needed. For best results the solution should be used within 24 hours.

IP Preparation:

A 1 quart jar is charged with 338.6 g of acetochlor technical (95.4%) preheated to 50° C. Then, 5.51 g of Furilazole safener (98%) are added and stirred until dissolved. This represents a 60:1 acetochlor:safener ratio in the core solution. To this homogeneous solution, 27.9 g of Norpar 15 are added. The two isocyanates are then weighed into the jar; 20.4 g of Desmodur N3200 and 4.1 g m-TMXDI. The solution is agitated to obtain a clear, homogeneous solution. The sealed jar is then placed in a 50° C. oven until needed. The solution should be used within 8 hours. The isocyanate composition is a blend of 77% (by equivalents) N3200 and 23% TMXDI.

Emulsification

The EP is added to a commercial Waring blender cup that has been preheated to 50° C. The commercial Waring blender (Waring Products Division, Dynamics Corporation of America, New Hartford, Conn., Blender 700) is powered through a 0–140 volt variable autotransformer. With the transformer at 60 volts, the IP is added to the EP over a 15 second interval. Within 5 seconds the speed of the blender is increased by increasing the voltage to 110, this speed is maintained for 20 seconds (time=0). The emulsion is transferred to a two liter beaker on a hot plate and stirred.

Cure:

Within 3 minutes after emulsification, 5.39 g of TETA in 5.2 g water is added to the stirred emulsion. The beaker is covered and the temperature is maintained at 50° C. for 2 hours, at which time the isocyanate infrared absorbance peak at 2270 cm$^{-1}$ is essentially gone.

Formulation:

To the slurry, 8.1 g of glycerol, 44.4 g of Irgasol DA liquid, 4.3 g of Lattice NTC70 (a microcrystalline cellulose from FMC), 10.1 g of a 4.7% aqueous solution of Proxel, and 0.32 g of Kelzan K8C241 were added. After allowing thirty minutes to dissolve the Kelzan, the formulation was completed with the addition of 8.85 g of disodium phosphate (anhydrous). The median particle size was 4.1 microns. The wall is a blend of 23% (by equivalents) TMXDI and 77% Desmodur N3200 cured with TETA at an 8% wall to core ratio.

While stirring this mixture, 46.5 g of a clear solution containing 44.98 g acetochlor and 1.52 g of Furilazole, which has been previously dissolved therein, is added to the vortex. The final formula contains 42% acetochlor, 5% as free acetochlor and 37% as encapsulated acetochlor. The longevity is not adversely effected, as can be seen in the following test.

Bioefficacy Results for Controlled Release Greenhouse Test—Length of Control

Figure 9:
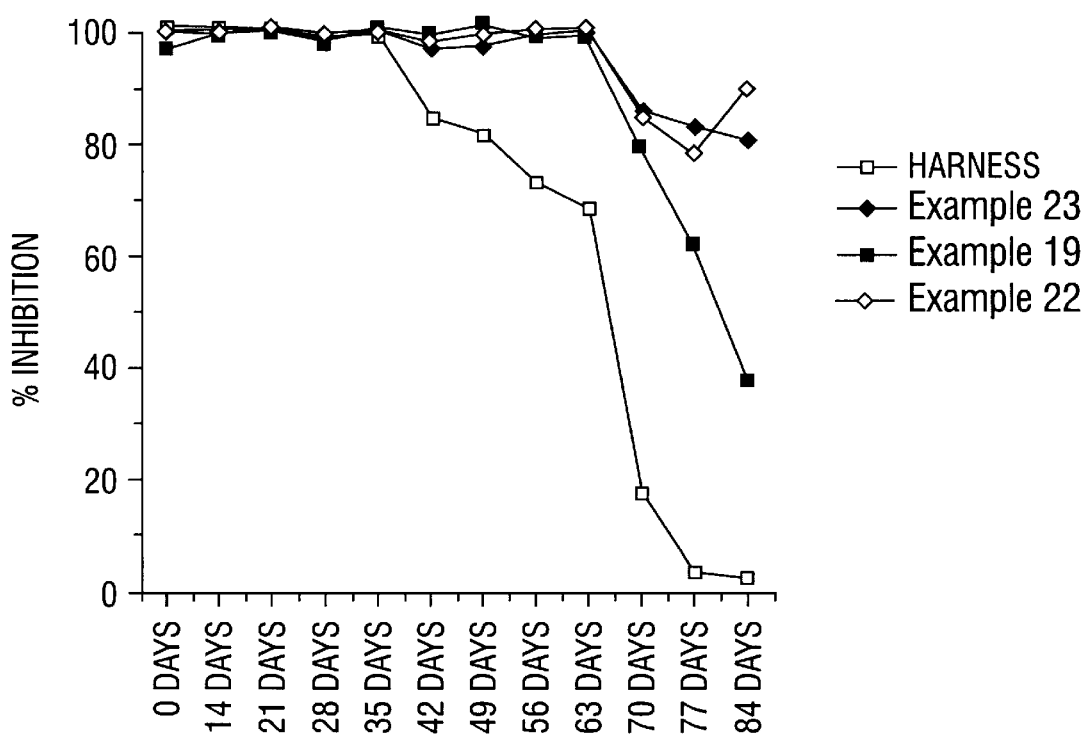
FIG. 9 is a graph of the herbicidal inhibition of several acetochlor formulations as a function of time.

The procedure described above was used to determine the length of control that the compositions of Examples 19, 22, and 23 would provide. As can be seen in FIG. 9, the acetochlor EC (Harness) provided 80% weed control out to only 49 days. Example 19 maintained 80% control of the weeds for 70 days, while Examples 22 and 23 were still at 80% control at the end of the test after 84 days.

Various U.S. patents have been mentioned in this specification. Each of those patents is incorporated here by reference.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for the preparation of a microencapsulated composition, comprising:

(a) combining (i) a triisocyanate that is an adduct of linear aliphatic isocyanates having the formula $$O=C=N-(CH_2)_n-N=C=O$$

where n is from about 4–18, (ii) an aliphatic diisocyanate that contains a cycloaliphatic or aromatic ring moiety, the aliphatic diisocyanate having from about 6–32 carbon atoms, and (iii) a water-immiscible composition comprising a core chemical;

(b) adding an aqueous liquid and forming an oil-in-water emulsion;

(c) adding a polyamine to the emulsion; and (d) reacting the triisocyanate, the diisocyanate, and the polyamine, thereby producing a plurality of microcapsules having a capsule wall, with at least a major portion of the core chemical encapsulated within the capsule wall of the microcapsules.

2. The process of claim 1, where the core chemical comprises a herbicide.

3. The process of claim 2, where the herbicide is an acetanilide.

4. The process of claim 2, where the herbicide is selected from the group consisting of alachlor, acetochlor, and butachlor.

5. The process of claim 1, where the core chemical comprises a first agricultural chemical, and where the water-immiscible composition further comprises and a second agricultural chemical.

6. The process of claim 5, where the first agricultural chemical is a herbicide and the second agricultural chemical is a safener.

7. The process of claim 1, where the triisocyanate has the formula

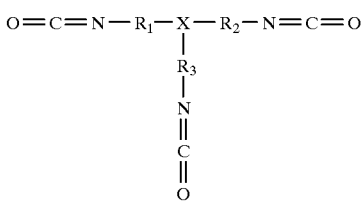

where $R_1$, $R_2$, and $R_3$ are independently alkyl groups having from 1–18 carbon atoms; and where X is a coupling agent selected from the group consisting of tertiary carbon, polycarbodiimide, polyurethane derived from an aliphatic alcohol or polyol, or combinations thereof.

8. The process of claim 1, where the triisocyanate is selected from the group consisting of

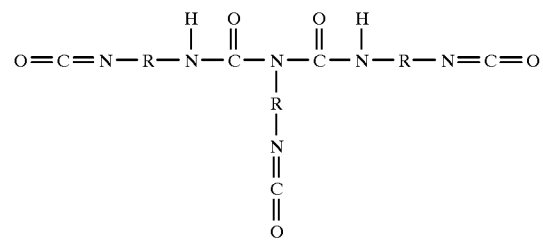

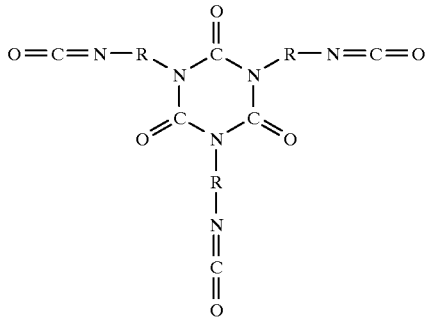

and

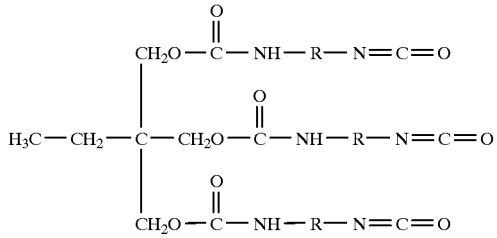

where R is $-(CH_2)_n-$, and where n is from about 4–18.

9. The process of claim 1, where the diisocyanate has from about 8–18 carbon atoms.

10. The process of claim 1, where the diisocyanate has the formula $$O=C=N-R^4-R^5-R^6-N=C=O$$

where $R^4$ and $R^6$ are independently aliphatic groups having 0–6 carbon atoms; and where $R^5$ comprises at least one substituted or unsubstituted cycloaliphatic or aromatic group having from 5–13 carbon atoms.

11. The process of claim 1, where the diisocyanate is selected from the group consisting of meta-tetramethylxylylene diisocyanate, 4,4'-diisocyanato-dicyclohexyl methane, and isophorone diisocyanate.

12. The process of claim 1, where the polyamine is selected from the group consisting of diethylene triamine, triethylene tetraamine, iminobispropylamine, bis(hexamethylene)triamine, polyoxypropylenetriamines, amine epoxy adducts, and alkyl diamines in which the alkyl group has from about 2–6 carbon atoms.

13. The process of claim 1, where the ratio of triisocyanate to diisocyanate is selected to provide a desired release rate from the microcapsules.

14. The process of claim 1, where the reaction of step (d) is performed by heating the mixture until the isocyanate infrared absorption peak at 2270 cm$^{-1}$ substantially disappears.

15. The process of claim 1, where the reaction of step (d) is performed by heating the mixture at between about 40–60° C. for between about 0.5–3 hours.

16. The process of claim 1, where the ratio of the triisocyanate to the diisocyanate, on an isocyanate equivalent basis, is between about 90:10 and about 30:70.

17. The process of claim 1, further comprising adding to the core chemical in step (a) a hydrophobic diluent.

18. The process of claim 16, where the hydrophobic diluent is selected from the group consisting of paraffinic oils having from about 12–28 carbon atoms, alkylated biphenyls, and naphthalenes.

19. A process for the preparation of a microencapsulated herbicidal composition, comprising:

(a) combining (i) a triisocyanate that is an adduct of linear aliphatic isocyanates having the formula

where n is from 4–18, (ii) an aliphatic diisocyanate that contains a cycloaliphatic or aromatic ring moiety, the aliphatic diisocyanate having from about 6–32 carbon atoms, and (iii) a water-immiscible composition comprising a herbicide;

(b) dispersing the mixture from step (a) in an aqueous liquid that contains a colloid, forming an oil-in-water emulsion;

(c) adding a polyamine to the emulsion; and (d) heating the mixture from step (c) at a temperature above about 40° C., thereby producing a plurality of microcapsules having a capsule wall, with at least a major portion of the agricultural chemical encapsulated within the capsule wall of the microcapsules.

20. The process of claim 19, where the herbicide is an acetanilide.

21. The process of claim 19, where the herbicide is selected from the group consisting of alachlor, acetochlor, and butachlor.

22. The process of claim 19, where the water-immiscible composition further comprises a safener.

23. The process of claim 19, where the triisocyanate has the formula

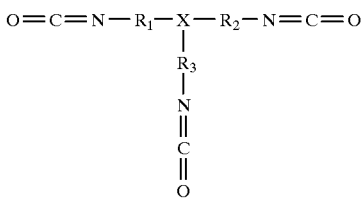

where $R_1$, $R_2$, and $R_3$ are independently alkyl groups having from i-18 carbon atoms; and where X is a coupling agent selected from the group consisting of tertiary carbon, polycarbodiimide, polyurethane derived from an aliphatic alcohol or polyol, or combinations thereof.

24. The process of claim 19, where the triisocyanate is selected from the group consisting of

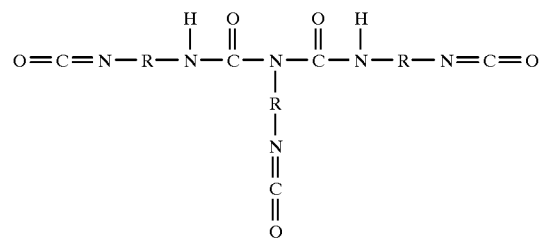

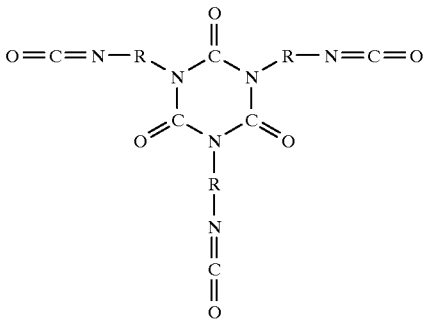

and

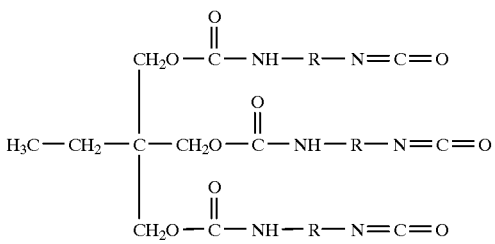

where R is —$(CH_2)_n$—, and where n is from about 4–18.

25. The process of claim 19, where the diisocyanate has from about 8–18 carbon atoms.

26. The process of claim 19, where the diisocyanate has the formula

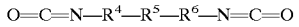

where $R^4$ and $R^6$ are independently aliphatic groups having 0–6 carbon atoms; and where $R^5$ comprises at least one substituted or unsubstituted cycloaliphatic or aromatic group having from 5–13 carbon atoms.

27. The process of claim 19, where the diisocyanate is selected from the group consisting of meta-tetramethylxylylene diisocyanate, 4,4'-diisocyanato-dicyclohexyl methane, and isophorone diisocyanate.

28. The process of claim 19, where the polyamine is selected from the group consisting of diethylene triamine, triethylene tetraamine, iminobispropylamine, bis(hexamethylene)triamine, polyoxypropylenetriamines, amine epoxy adducts, and alkyl diamines in which the alkyl group has from about 2–6 carbon atoms.

29. The process of claim 19, where the ratio of triisocyanate to diisocyanate is selected to provide a desired release rate from the microcapsules.

30. The process of claim 19, where the mixture is heated in step (d) until the isocyanate infrared absorption peak at 2270 cm$^{-1}$ substantially disappears.

31. The process of claim 19, where the mixture is heated in step (d) at between about 40–60° C. for between about 0.5–3 hours.

32. The process of claim 19, where the colloid is selected from the group consisting of gelatin, casein, polyvinyl alcohol, alkylated polyvinyl pyrrolidone polymers, maleic anhydride-methyl vinyl ether copolymers, styrene-maleic anhydride copolymers, maleic acid-butadiene copolymers, maleic anhydride-diisobutylene copolymers, sodium and calcium lignosulfates, sulfonated naphthalene-formaldehyde condensates, modified starches, and modified cellulose.

33. The process of claim 19, where the ratio of the triisocyanate to the diisocyanate, on a cyanate equivalent basis, is between about 90:10 and about 30:70.

34. The process of claim 19, further comprising adding to the agricultural chemical in step (a) a hydrophobic diluent.

35. The process of claim 34, where the hydrophobic diluent is selected from the group consisting of paraffinic oils having from about 12-28 carbon atoms, alkylated biphenyls, and naphthalenes.

36. A selective-release microencapsulated composition, comprising a plurality of microcapsules, the microcapsules comprising:
(a) a capsule wall that comprises the polymerization product of:
  (i) a triisocyanate that is an adduct of linear aliphatic isocyanates having the formula

where n is from 4–18,
  (ii) an aliphatic diisocyanate that contains a cycloaliphatic or aromatic ring moiety, the aliphatic diisocyanate having from about 6–32 carbon atoms, and
  (iii) a polyamine; and
(b) an internal phase encapsulated within the capsule wall that comprises a first core chemical and a second core chemical, where the first core chemical has a different rate of release from the microcapsules than the second core chemical.

37. The composition of claim 36, where the internal phase further comprises a hydrophobic diluent.

38. The composition of claim 37, where the hydrophobic diluent is selected from the group consisting of paraffinic oils having from about 12–28 carbon atoms, alkylated biphenyls, and naphthalenes.

39. The composition of claim 36, where the first core chemical is a herbicide and the second core chemical is a safener.

40. The composition of claim 36, where the first core chemical is an acetanilide herbicide and the second core chemical is a safener.

41. The composition of claim 40, where the safener is furilazole.

42. The composition of claim 36, where the triisocyanate has the formula

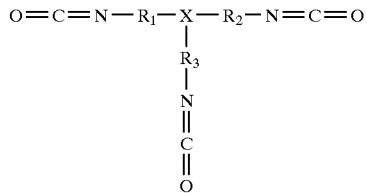

where $R_1$, $R_2$, and $R_3$ are independently alkyl groups having from 1–18 carbon atoms; and where X is a coupling agent selected from the group consisting of tertiary carbon, polycarbodiimide, polyurethane derived from an aliphatic alcohol or polyol, or combinations thereof.

43. The composition of claim 36, where the triisocyanate is selected from the group consisting of

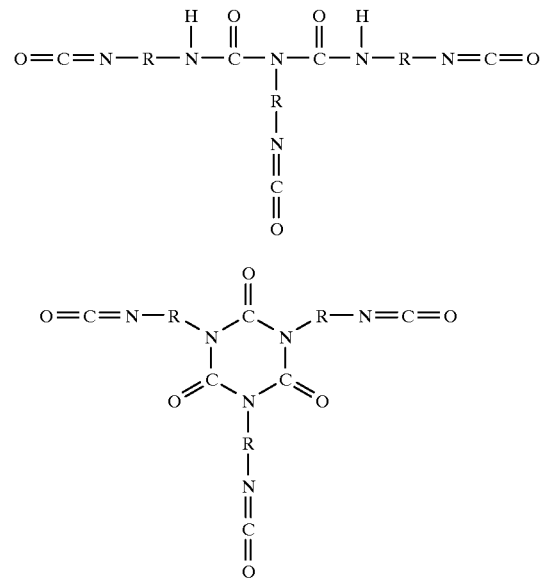

and

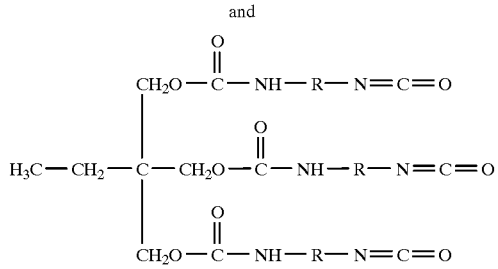

where R is —$(CH_2)_n$—, and where n is from about 4–18.

44. The composition of claim 36 where the diisocyanate has the formula

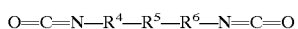

where $R^4$ and $R^6$ are independently aliphatic groups having 0–6 carbon atoms; and where $R^5$ comprises at least one substituted or unsubstituted cycloaliphatic or aromatic group having from 5–13 carbon atoms.

45. The composition of claim 36, where the diisocyanate is selected from the group consisting of meta-tetramethylxylylene diisocyanate, 4,4'-diisocyanato-dicyclohexyl methane, and isophorone diisocyanate.

46. The composition of claim 36, where the polyamine is selected from the group consisting of diethylene triamine, triethylene tetraamine, iminobispropylamine, bis(hexamethylene)triamine, polyoxypropylenetriamines, amine epoxy adducts, and alkyl diamines in which the alkyl group has from about 2–6 carbon atoms.

47. The composition of claim 36, where the triisocyanate and the diisocyanate are used in a ratio that is selected to provide a desired release rate from the microcapsules.

48. The composition of claim 36, where the ratio of the triisocyanate to the diisocyanate, on a cyanate equivalent basis, is between about 90:10 and about 30:70.

49. A microencapsulated herbicide composition, comprising an aqueous dispersion of microcapsules, the microcapsules comprising:
(a) a capsule wall that comprises the polymerization product of:
(i) a triisocyanate that is an adduct of linear aliphatic isocyanates having the formula

where n is from 4–18,
(ii) an aliphatic diisocyanate that contains a cycloaliphatic or aromatic ring moiety, the aliphatic diisocyanate having from about 6–32 carbon atoms, and
(iii) a polyamine; and
(b) an internal phase that comprises a herbicide and is encapsulated within the capsule wall.

50. The composition of claim 49, where the herbicide is an acetanilide.

51. The composition of claim 49, where the herbicide is selected from the group consisting of alachlor, acetochlor, and butachlor.

52. The composition of claim 49, where the internal phase further comprises a safener.

53. The composition of claim 49, where the safener is more soluble in the capsule wall than the herbicide.

54. The composition of claim 49, where the safener has a smaller molecular size than the herbicide.

55. The composition of claim 49, where the triisocyanate has the formula

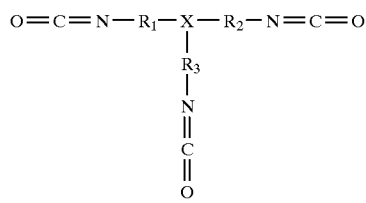

where $R_1$, $R_2$, and $R_3$ are independently alkyl groups having from 1–18 carbon atoms; and
where X is a coupling agent selected from the group consisting of tertiary carbon, polycarbodiimide, polyurethane derived from an aliphatic alcohol or polyol, or combinations thereof.

56. The composition of claim 49, where the triisocyanate is selected from the group consisting of

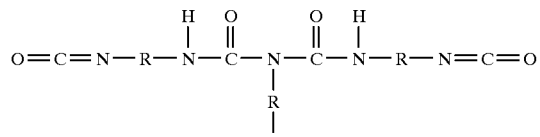

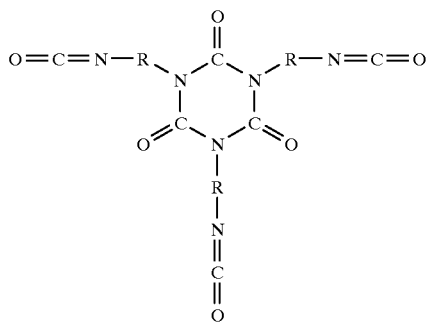

and

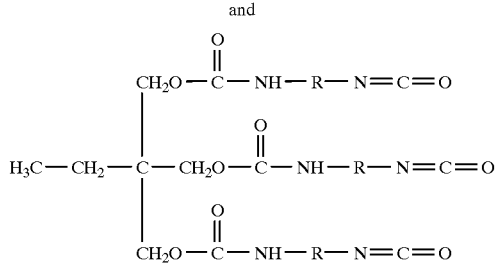

where R is 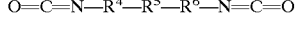, and where n is from about 4–18.

57. The composition of claim 49, where the diisocyanate has from about 8–18 carbon atoms.

58. The composition of claim 49, where the diisocyanate has the formula $$O=C=N-R^4-R^5-R^6-N=C=O$$

where $R^4$ and $R^6$ are independently aliphatic groups having 0–6 carbon atoms; and
where $R^5$ comprises at least one substituted or unsubstituted cycloaliphatic or aromatic group having from 5–13 carbon atoms.

59. The composition of claim 49, where the diisocyanate is selected from the group consisting of meta-tetramethylxylylene diisocyanate, 4,4'-diisocyanato-dicyclohexyl methane, and isophorone diisocyanate.

60. The composition of claim 49, where the polyamine is selected from the group consisting of diethylene triamine, triethylene tetraamine, iminobispropylamine, and bis(hexamethylene)triamine, polyoxypropylenetriamines, amine epoxy adducts, and alkyl diamines in which the alkyl group has from about 2–6 carbon atoms.

61. The composition of claim 49, where the ratio of triisocyanate to diisocyanate is selected to provide a desired release rate from the microcapsules.

62. The composition of claim 49, where the composition is a liquid concentrate that is suitable for spraying onto plants, soil, or a growth medium after dilution with water.

63. The composition of claim 49, where the composition is a spray solution that is suitable for spraying onto plants, soil, or growth medium without further dilution with water.

64. The composition of claim 49, where the ratio of the triisocyanate to the diisocyanate, on a cyanate equivalent basis, is between about 90:10 and about 30:70.

65. The composition of claim 49, where the internal phase further comprises a hydrophobic diluent.

66. The composition of claim 49, where the hydrophobic diluent is selected from the group consisting of paraffinic oils having from about 12–28 carbon atoms, alkylated biphenyls, and naphthalenes.

67. A microencapsulated herbicide composition, comprising a plurality of microcapsules, the microcapsules comprising:
(a) a capsule wall that comprises the polymerization product of:
(i) a triisocyanate that is an adduct of linear aliphatic isocyanates having the formula O=C=N—(CH$_2$)$_n$—N=C=O where n is from 4–18,
(ii) an aliphatic diisocyanate that contains a cycloaliphatic or aromatic ring moiety, the aliphatic diisocyanate having from about 6–32 carbon atoms, and
(iii) a polyamine; and
(b) an internal phase that comprises
(i) a herbicide selected from the group consisting of alachlor, acetochlor, and butachlor;
(ii) furilazole in an amount effective to protect desirable crops from herbicidal effects of the herbicide; and
(iii) a hydrophobic diluent selected from selected from the group consisting of paraffinic oils having from about 12–28 carbon atoms, alkylated biphenyls, and naphthalenes.

68. A herbicidal method, comprising applying to a plant, soil, or a growth medium a herbicidally effective amount of a composition that comprises an aqueous dispersion of microcapsules, the microcapsules comprising:
(a) a capsule wall that comprises the polymerization product of:
(i) a triisocyanate that is an adduct of linear aliphatic isocyanates having the formula O=C=N—(CH$_2$)$_n$—N=C=O where n is from 4–18,
(ii) an aliphatic diisocyanate that contains a cycloaliphatic or aromatic ring moiety, the aliphatic diisocyanate having from about 6–32 carbon atoms, and
(iii) a polyamine
(b) an internal phase that comprises a herbicide and is encapsulated within the capsule wall.

69. The method of claim 68, where the herbicide is an acetanilide.

70. The method of claim 68, where the herbicide is selected from the group consisting of alachlor, acetochlor, and butachlor.

71. The method of claim 68, where the internal phase further comprises a safener.

72. The method of claim 68, where the safener is more soluble in the capsule wall than the herbicide.

73. The method of claim 68, where the safener has a smaller molecular size than the herbicide.

74. The method of claim 68, where the triisocyanate has the formula

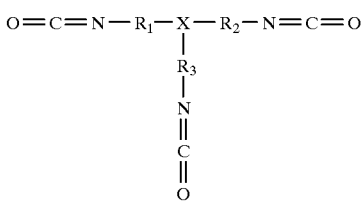

where $R_1$, $R_2$, and $R_3$ are independently alkyl groups having from 1–18 carbon atoms; and
where X is a coupling agent selected from the group consisting of tertiary carbon, polycarbodiimide, polyurethane derived from an aliphatic alcohol or polyol, or combinations thereof.

75. The method of claim 68, where the triisocyanate is selected from the group consisting of

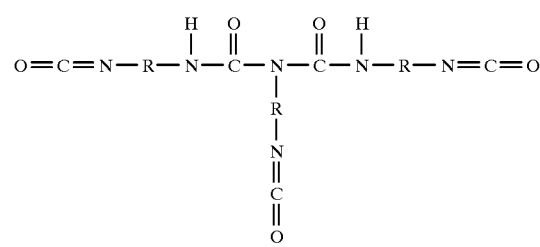

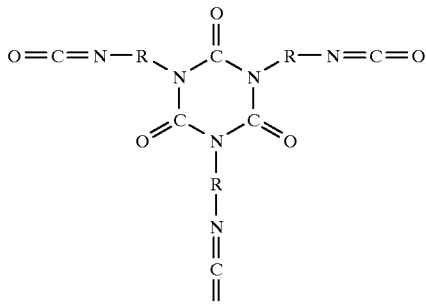

and

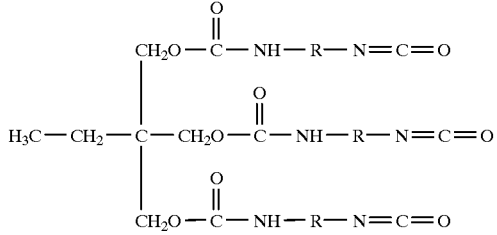

where R is —(CH$_2$)$_n$—, and where n is from about 4–18.

76. The method of claim 68, where the diisocyanate has from about 8–18 carbon atoms.

77. The method of claim 68, where the diisocyanate has the formula

O=C=N—R$^4$—R$^5$—R$^6$—N=C=O where R$^4$ and R$^6$ are independently aliphatic groups having 0–6 carbon atoms; and
where R$^5$ comprises at least one substituted or unsubstituted cycloaliphatic or aromatic group having from 5–13 carbon atoms.

78. The method of claim 68, where the diisocyanate is selected from the group consisting of meta-tetramethylxylylene diisocyanate, 4,4'-diisocyanato-dicyclohexyl methane, and isophorone diisocyanate.

79. The method of claim 68, where the polyamine is selected from the group II consisting of diethylene triamine, triethylene tetraamine, iminobispropylamine, and bis(hexamethylene)triamine, polyoxypropylenetriamines, amine epoxy adducts, and alkyl diamines in which the alkyl group has from about 2–6 carbon atoms.

80. The method of claim 68, where the ratio of triisocyanate to diisocyanate is selected to provide a desired release rate from the microcapsules.

81. The method of claim 68, where the ratio of the triisocyanate to the diisocyanate, on a cyanate equivalent basis, is between about 90:10 and about 30:70.

82. The method of claim 68, where the internal phase further comprises a hydrophobic diluent.

83. The method of claim 82, where the hydrophobic diluent is selected from the group consisting of paraffinic oils having from about 12–28 carbon atoms, alkylated biphenyls, and naphthalenes.

84. A herbicidal method, comprising applying to a plant, soil, or a growth medium a herbicidally effective amount of a composition that comprises an aqueous dispersion of microcapsules, the microcapsules comprising:
   (a) a capsule wall that comprises the polymerization product of:
      (i) a triisocyanate that is an adduct of linear aliphatic isocyanates having the formula

$$O=C=N-(CH_2)_n-N=C=O$$

where n is from 4–18,
      (ii) an aliphatic diisocyanate that contains a cycloaliphatic or aromatic ring moiety, the aliphatic diisocyanate having from about 6–32 carbon atoms, and
      (iii) a polyamine; and
   (b) an internal phase that comprises
      (i) a herbicide selected from the group consisting of alachlor, acetochlor, and butachlor;
      (ii) furilazole in an amount effective to protect desirable crops from herbicidal effects of the herbicide; and
      (iii) a hydrophobic diluent selected from selected from the group consisting of paraffinic oils having from about 12–28 carbon atoms, alkylated biphenyls, and naphthalenes.

85. A method of controlling weeds in a field containing both weeds and crops, comprising applying to a field an amount effective to provide herbicidal control of the weeds in that field of a plurality of microcapsules, the microcapsules comprising:
   (a) a capsule wall that comprises the polymerization product of:
      (i) a triisocyanate that is an adduct of linear aliphatic isocyanates having the formula

$$O=C=N-(CH_2)_n-N=C=O$$

where n is from 4–18,
      (ii) an aliphatic diisocyanate that contains a cycloaliphatic or aromatic ring moiety, the aliphatic diisocyanate having from about 6–32 carbon atoms, and
      (iii) a polyamine
   (b) an internal phase that is encapsulated within the capsule wall and that comprises:
      (i) a herbicide, and
      (ii) a chemical antidote for the herbicide, in an amount effect to protect the crops from the herbicidal effects of the herbicide, where the chemical antidote is released initially from the microcapsules at a greater rate than the herbicide.

86. The method of claim 85, where the herbicide is an acetanilide.

87. The method of claim 85, where the herbicide is selected from the group consisting of alachlor, acetochlor, and butachlor.

88. The method of claim 85, where the chemical antidote is more soluble in the capsule wall than the herbicide.

89. The method of claim 85, where the chemical antidote has a smaller molecular size than the herbicide.

90. The method of claim 85, where the triisocyanate has the formula

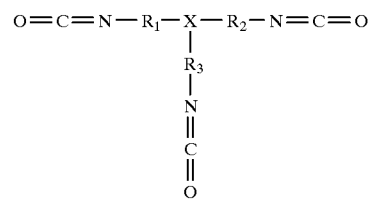

where $R_1$, $R_2$, and $R_3$ are independently alkyl groups having from 1–18 carbon atoms; and where X is a coupling agent selected from the group consisting of tertiary carbon, polycarbodiimide, polyurethane derived from an aliphatic alcohol or polyol, or combinations thereof.

91. The method of claim 85, where the triisocyanate is selected from the group consisting of

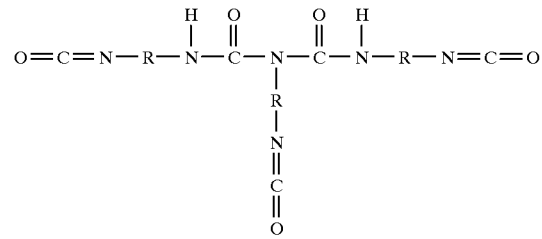

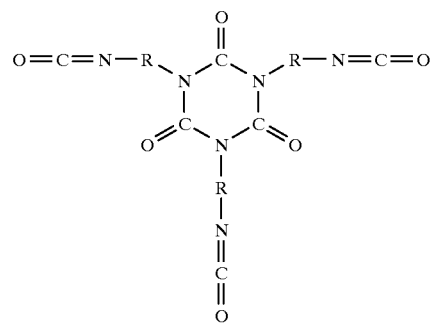

-continued and

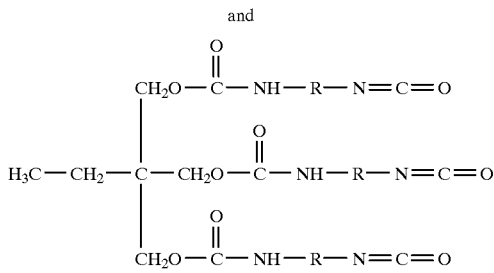

where R is $-(CH_2)_n-$, and where n is from about 4–18.

92. The method of claim 85, where the diisocyanate has from about 8–18 carbon atoms.

93. The method of claim 85, where the diisocyanate has the formula $$O=C=N-R^4-R^5-R^6-N=C=O$$

where $R^4$ and $R^6$ are independently aliphatic groups having 0–6 carbon atoms; and where $R^5$ comprises at least one substituted or unsubstituted cycloaliphatic or aromatic group having from 5–13 carbon atoms.

94. The method of claim 85, where the diisocyanate is selected from the group consisting of meta-tetramethylxylylene diisocyanate, 4,4'-diisocyanato-dicyclohexyl methane, and isophorone diisocyanate.

95. The method of claim 85, where the polyamine is selected from the group consisting of diethylene triamine, triethylene tetraamine, iminobispropylamine, and bis (hexamethylene)triamine, polyoxypropylenetriamines, amine epoxy adducts, and alkyl diamines in which the alkyl group has from about 2–6 carbon atoms.

96. The method of claim 85, where the ratio of triisocyanate to diisocyanate is selected to provide a desired release rate from the microcapsules.

97. The method of claim 85, where the ratio of the triisocyanate to the diisocyanate, on a cyanate equivalent basis, is between about 90:10 and about 30:70.

98. The method of claim 85, where the internal phase further comprises a hydrophobic diluent.

99. The method of claim 98, where the hydrophobic diluent is selected from the group consisting of paraffinic oils having from about 12–28 carbon atoms, alkylated biphenyls, and naphthalenes.

* * * * *